(12) United States Patent
Miki et al.

(10) Patent No.: US 10,426,185 B2
(45) Date of Patent: Oct. 1, 2019

(54) TASTE SUBSTANCE-SUPPLYING ARTICLE

(71) Applicant: KEIO UNIVERSITY, Minato-ku, Tokyo (JP)

(72) Inventors: Norihisa Miki, Yokohama (JP); Kazuhiko Higashi, Yokohama (JP)

(73) Assignee: KEIO UNVERSITY, Tokyo (JP)

( * ) Notice: Subject to any disclaimer, the term of this patent is extended or adjusted under 35 U.S.C. 154(b) by 0 days.

(21) Appl. No.: 15/317,395

(22) PCT Filed: Jun. 3, 2015

(86) PCT No.: PCT/JP2015/066037
§ 371 (c)(1),
(2) Date: Dec. 8, 2016

(87) PCT Pub. No.: WO2015/190366
PCT Pub. Date: Dec. 17, 2015

(65) Prior Publication Data
US 2018/0020710 A1    Jan. 25, 2018

(30) Foreign Application Priority Data
Jun. 11, 2014 (JP) .................. 2014-120688

(51) Int. Cl.
*A23L 27/00* (2016.01)
*A61J 7/00* (2006.01)
(Continued)

(52) U.S. Cl.
CPC ............. *A23L 27/88* (2016.08); *A61J 7/0092* (2013.01); *A23V 2002/00* (2013.01); *A61C 7/10* (2013.01);
(Continued)

(58) Field of Classification Search
CPC ........... A23L 27/88; A61C 7/12; A61C 13/08; A23V 2002/00
See application file for complete search history.

(56) References Cited

U.S. PATENT DOCUMENTS 3,503,127 A    3/1970  Kasdin et al.
4,175,326 A    11/1979 Goodson
(Continued)

FOREIGN PATENT DOCUMENTS

JP    S58001423 U    1/1983
JP    05500018 A     1/1993
(Continued)

OTHER PUBLICATIONS

International Search Report (ISR) dated Jul. 14, 2015 and Written Opinion issued in International Application No. PCT/JP2015/066037.
(Continued)

*Primary Examiner* — Donnell A Long
(74) *Attorney, Agent, or Firm* — Holtz, Holtz & Volek PC

(57) ABSTRACT

A taste substance-supplying article is provided with: a taste substance-supplying body having a taste substance that is brought into contact with taste receptors to produce a sense of taste, and a taste-releasing part that retains the taste substance and gradually releases the taste substance; and a fixing part that fixes the taste substance-supplying body to an oral cavity so that the taste-releasing part can be brought into contact with a portion of an area being a part of the oral cavity and having taste receptors. The taste-releasing part is brought into contact with taste receptors, and supplies and causes the taste substance to come into contact with the taste receptors.

5 Claims, 11 Drawing Sheets

(51) Int. Cl.
 *A61C 7/10* (2006.01)
 *A61C 19/06* (2006.01)
 *A61M 31/00* (2006.01)
 *A61C 7/12* (2006.01)
 *A61C 13/08* (2006.01)

(52) U.S. Cl.
 CPC ............... *A61C 7/12* (2013.01); *A61C 13/08* (2013.01); *A61C 19/063* (2013.01); *A61M 31/002* (2013.01)

(56) References Cited

U.S. PATENT DOCUMENTS

| | | | |
|---|---|---|---|
| 4,741,700 A | 5/1988 | Barabe | |
| 4,861,268 A | 8/1989 | Garay et al. | |
| 5,395,392 A | 3/1995 | Suhonen | |
| 2003/0046954 A1 | 3/2003 | Ashton | |
| 2008/0182218 A1 | 7/2008 | Chen et al. | |
| 2012/0109051 A1* | 5/2012 | Harrell | A61F 5/0006 604/77 |
| 2013/0296751 A1 | 11/2013 | Martin et al. | |
| 2014/0121594 A1* | 5/2014 | Connor | A61F 5/0006 604/77 |

FOREIGN PATENT DOCUMENTS

| | | |
|---|---|---|
| JP | 3158108 U | 3/2010 |
| JP | 2011254782 A | 12/2011 |
| JP | 2014038025 A | 2/2014 |
| WO | 2007140784 A2 | 12/2007 |
| WO | 2013144710 A1 | 10/2013 |

OTHER PUBLICATIONS

Nimesha Ranasinghe et al., "Tongue Mounted Interface for Digitally Actuating the Sense of Taste", 16th International Symposium on Wearable Computers (2012), pp. 80-87.

Yoshie Kanazawa, "Jinko Toseki Kanja no Shokuen Mikaku to Shokuji Kanri", The Japanese Journal of Clinical Nutrition, vol. 100, No. 5, May 2002, pp. 564-566.

Extended European Search Report (EESR) dated Dec. 15, 2017 issued in counterpart European Application No. 15807530.9.

Japanese Office Action dated Sep. 18, 2018 (and English translation thereof) issued in counterpart Japanese Application No. 2016-527764.

European Office Action dated Feb. 14, 2019 issued in counterpart European Application No. 15807530.9.

* cited by examiner

TASTE SUBSTANCE-SUPPLYING ARTICLE

TECHNICAL FIELD

The present invention relates to a taste substance-supplying article which supplies a taste substance to the taste receptors when a food or drink is taken to the oral cavity, and synthesizes the taste from the taste substance and the taste of the food or drink, so as to enable the user to enjoy the taste.

BACKGROUND ART

Traditionally, like dialysis patients or diabetic patients, a person under a dietary restriction of a taste substance such as salt or sugar must take a food or drink with extremely low salt and sugar contents. Accordingly, the person cannot sufficiently enjoy a taste such as a salty taste as he or she desires. Meanwhile, it is known that an electrode is brought into contact with intraoral taste receptors, and then electricity is applied from the electrode to the taste receptors, so that the person can sense the taste without taking the relevant taste substance (see non-patent document 1). In addition, candies and the like that do not cause any sudden increase in blood glucose level have been proposed (see patent document 1).

Patent Document 1: Japanese Unexamined Patent Application, Publication No. 2011-254782

Non-Patent Document 1: Nimesha Ranasinghe et al., Tongue Mounted Interface for Digitally Actuatinog the Sense of Taste, 16th International Symposium on Wearable Computers, (2012), pp. 80-87

DISCLOSURE OF THE INVENTION

Problems to be Solved by the Invention

Within the oral cavity, taste receptors that sense salty taste, sweet taste, sour taste, and umami, respectively, are tightly packed within narrow ranges. Therefore, as described above, when electricity is applied from an electrode to taste receptors for a person to sense a taste without taking any taste substance, electricity is applied from the electrode to taste receptors that respectively sense salty taste, sweet taste, sour taste, and umami, at the same time. This causes a problem such that only a bitter taste is sensed as a whole.

The present invention has been achieved in view of such a problem, and relates to a taste substance-supplying article, which enables a person to enjoy the taste of a taste substance, when the person takes a food or drink with an extremely low content of the taste substance into the oral cavity.

Means for Solving the Problems

The present invention relates to a taste substance-supplying article, which is provided with: a taste substance-supplying body having a taste substance that is brought into contact with taste receptors to produce a sense of taste, and a taste-releasing part for retaining the taste substance and gradually releasing the taste substance; and a fixing part that fixes the taste substance-supplying body to the oral cavity, so that the taste-releasing part can be brought into contact with a portion of an area being a part of the oral cavity and having taste receptors, by which the taste-releasing part is brought into contact with the taste receptors and supplies and causes the taste substance into contact with the taste receptors.

Furthermore, preferably the taste substance-supplying body is provided with a taste substance reservoir part having a reservoir space that can accommodate the taste substance and the taste-releasing part, wherein the taste-releasing part gradually releases the taste substance accommodated within the reservoir space from the reservoir space to the outside of the reservoir space, and the fixing part is supported by a part of the oral cavity, and is provided with a reservoir part-supporting part for supporting the taste substance reservoir part in the oral cavity such that the taste-releasing part can be brought into contact with taste receptors in the oral cavity.

Furthermore, preferably the taste substance-reservoir part has a reservoir having an opening, wherein the reservoir space is composed of the internal space of the reservoir, and the taste-releasing part is disposed at the opening so as to cover the opening.

Furthermore, the taste-releasing part is preferably composed of a porous membrane.

Furthermore, preferably the taste substance-reservoir part has a reservoir having an opening, wherein the reservoir space is composed of the internal space of the reservoir, the taste-releasing part is composed of the opening and a porous material disposed in the reservoir space, and a taste substance is impregnated with the porous material.

Furthermore, preferably the reservoir can be deformed so that the capacity of the reservoir space can be varied.

Furthermore, preferably the taste substance reservoir part is fixed to one end of the reservoir part-supporting part, and the other end of the reservoir part-supporting part is fixed to an attachment member that is fixed to a part of the oral cavity.

Furthermore, preferably the taste substance reservoir part is fixed to the central part of the reservoir part-supporting part, one end of the reservoir part-supporting part is fixed to an attachment member that is fixed to a part of the oral cavity, and the other end of the reservoir part-supporting part is fixed to an attachment member that is fixed to a portion other than the part of the oral cavity.

Furthermore, preferably the attachment member is composed of a dental brace that is fixed to the upper jaw, and the taste-releasing part is brought into contact with the taste receptors of the palate.

Furthermore, preferably the attachment member is composed of a false tooth that is fixed to the upper jaw, and the taste-releasing part is brought into contact with the taste receptors of the palate.

Furthermore, preferably the taste substance reservoir part is fixed to one end of the reservoir part-supporting part, and the other end of the reservoir part-supporting part is fixed to a part of the oral cavity.

Furthermore, preferably the taste substance reservoir part is fixed to the central part of the reservoir part-supporting part, one end of the reservoir part-supporting part is fixed to a part of the oral cavity, and the other end of the reservoir part-supporting part is fixed to a portion other than the part of the oral cavity.

Furthermore, preferably the reservoir part-supporting part is a cyclic portion having one end and the other end, wherein the taste substance reservoir part is fixed to the central part of the reservoir part-supporting part, the reservoir part-supporting part and the taste substance reservoir part are fixed to the tongue, so that the reservoir part-supporting part and the taste substance reservoir part wrap around the tongue, and the taste-releasing part is brought into contact with the taste receptors on the top surface of the tongue.

Furthermore, preferably provided are: a taste releasing part-changing drive part for changing the taste-releasing part in a manner such that a taste substance accommodated within the reservoir space is gradually released from the taste-releasing part; a food or drink-detecting part capable of detecting the intake of a food or drink into the oral cavity by a user of a taste substance-supplying article through detection of at least one of the chewing of the taste substance-supplying article by a user, the intake of a food or drink into the oral cavity of the user of the taste substance-supplying article, a change in intraoral potential of the user of the taste substance-supplying article, and a change in intraoral temperature of the user of the taste substance-supplying article; and a control part for controlling the taste releasing part-changing drive part, so as to initiate the release of a taste substance accommodated within the reservoir space from the reservoir space to the outside of the reservoir space, when the food or drink-detecting part detects the intake of a food or drink into the oral cavity by the user of the taste substance-supplying article.

Furthermore, preferably the fixing part is composed of a cohesive substance. Furthermore, preferably the taste substance-supplying body is fixed to a portion of an area being a part of the oral cavity and having taste receptors, so as to cover the portion. Furthermore, preferably the taste substance-supplying body is net-shaped. Furthermore, preferably the taste-releasing part is disintegratable or dissolvable within the oral cavity.

Effects of the Invention

According to the present invention, a taste substance-supplying article can be provided, which enables a user to enjoy the taste of a taste substance when the user takes a food or drink with an extremely low content of the taste substance into the oral cavity.

PREFERRED MODE FOR CARRYING OUT THE INVENTION

Figure 1:
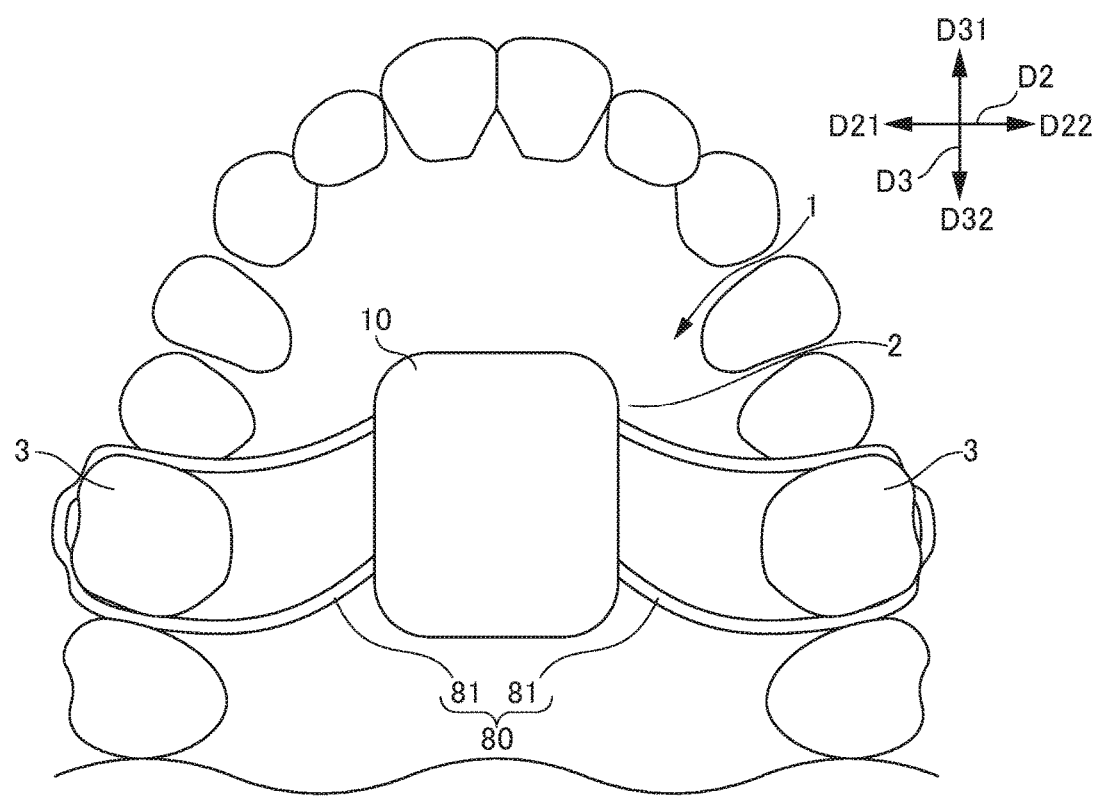
FIG. 1 is a schematic view showing how a reservoir part-supporting part 80 of a taste substance-supplying article 1 according to a $1^{st}$ embodiment of the present invention is fixed to teeth 3 of the upper jaw.
Figure 2:
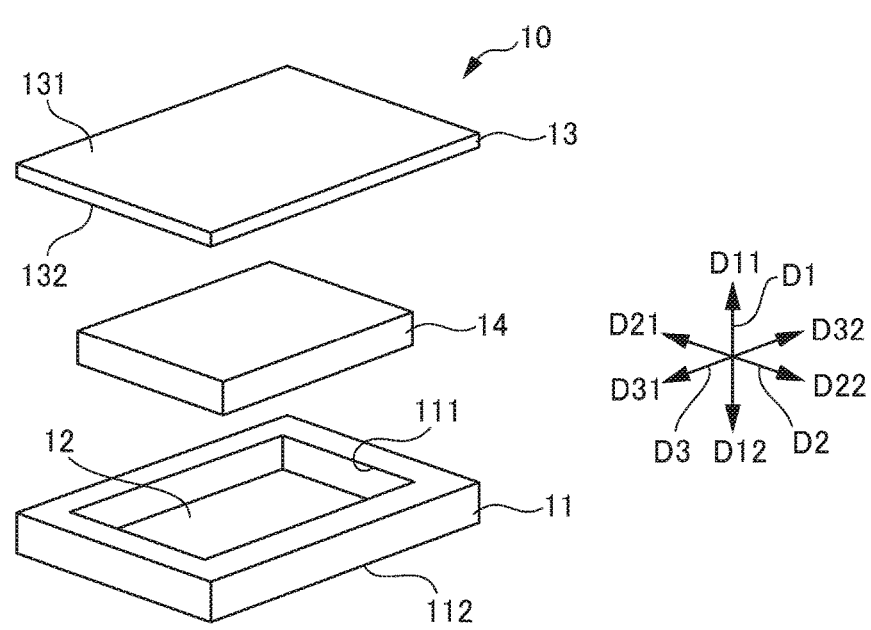
FIG. 2 is a schematic exploded perspective view showing a taste substance reservoir part 10 of the taste substance-supplying article 1 according to the $1^{st}$ embodiment of the present invention.
Figure 3:
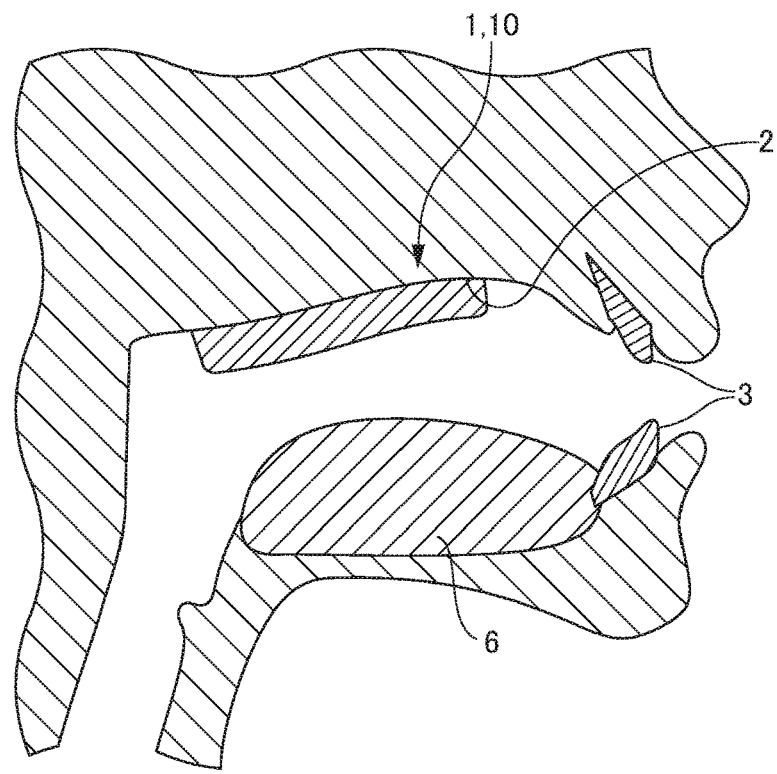
FIG. 3 is a schematic sectional view showing how the taste substance reservoir part 10 of the taste substance-supplying article 1 according to the $1^{st}$ embodiment of the present invention is fixed while being in contact to palate 2.
Figure 4:
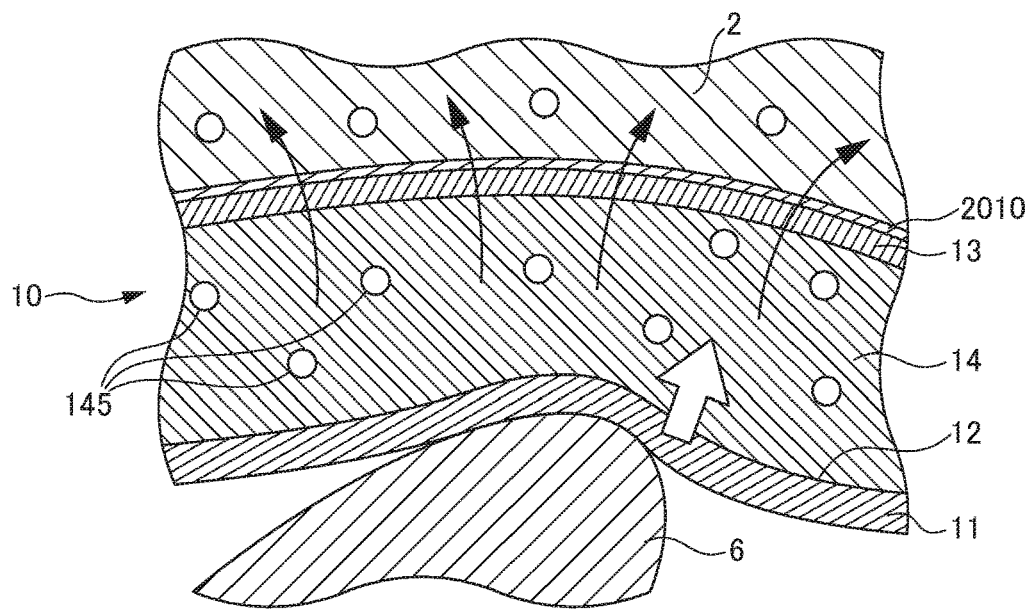
FIG. 4 is a schematic sectional view showing how salt as a taste substance 145 is released from a porous membrane 13 of the taste substance-supplying article 1 according to the $1^{st}$ embodiment of the present invention to taste receptors 2010 of palate 2.

Hereafter, the taste substance-supplying article 1 according to the $1^{st}$ embodiment of the present invention will be explained referring to FIG. 1 to FIG. 4. FIG. 1 is a schematic view showing how the reservoir part-supporting part 80 of the taste substance-supplying article 1 according to the $1^{st}$ embodiment of the present invention is fixed to teeth 3 of the upper jaw. FIG. 2 is a schematic exploded perspective view showing the taste substance reservoir part 10 of the taste substance-supplying article 1 according to the $1^{st}$ embodiment of the present invention. FIG. 3 is a schematic sectional view showing how the taste substance reservoir part 10 of the taste substance-supplying article 1 according to the $1^{st}$ embodiment of the present invention is fixed while being in contact with palate 2. FIG. 4 is a schematic sectional view showing how salt as the taste substance 145 is released from the porous membrane 13 of the taste substance-supplying article 1 according to the $1^{st}$ embodiment of the present invention to the taste receptors 2010 of palate 2.

As shown in FIG. 1, the taste substance-supplying article 1 is provided with the taste substance 145, the taste substance reservoir part 10, and the reservoir part-supporting part 80 as a fixing part. The taste substance reservoir part 10 has a reservoir 11, a reservoir space 12, the porous membrane 13 as a taste-releasing part, and a taste substance impregnated material 14. The taste substance 145 and the taste substance reservoir part 10 compose the taste substance-supplying body. The reservoir part-supporting part 80 has a pair of bridge parts 81.

Here, for convenience of explanation, the direction from a reservoir body 112 (see FIG. 2) as described below to the porous membrane 13 (upward direction in FIG. 2) is defined as an upward direction D11, a direction opposite to this direction is defined as a downward direction D12, and these directions are defined as a vertical direction D1. The direction (leftward direction in FIG. 1) from the right bridge part 81 to the left bridge part 81, as shown in FIG. 1, of the pair of bridge parts 81 described below is defined as a left upward direction D21, a direction opposite to this direction is defined as a right direction D22, and these directions are defined as a horizontal direction D2. In addition, an upward direction shown in FIG. 1, which is perpendicular to the vertical direction D1 and the horizontal direction D2 is defined as a forward direction D31, a direction opposite to this direction is defined as backward direction D32, and these directions are defined as a longitudinal direction D3. Hereafter, main figures contain arrows showing these directions.

The reservoir 11 has, as shown in FIG. 2, a reservoir body 112 that is box-shaped to have an approximately rectangular parallelepiped outside shape. The reservoir body 112 has an opening part 111 that opens upward, instead of the top wall of the box. The reservoir body 112 is composed of an elastically deformable material through which no taste substance 145 can pass, and composed of rubber, for example, in this embodiment. Accordingly, the reservoir body 112 of the reservoir 11 is deformable in its entirety, so that the capacity of the reservoir space 12 can be varied. The reservoir space 12 is composed of the internal space of the reservoir body 112 of the reservoir 11, so that the space can accommodate and retain the taste substance impregnated material 14 impregnated with the taste substance 145.

The porous membrane 13 is disposed at the opening part 111 to cover the opening of the opening part 111. The porous membrane 13 is composed of a semipermeable membrane, a reverse osmosis membrane (RO membrane), a porous membrane made of a shape-memory alloy, or the like. In this embodiment, the porous membrane 13 is composed of a permeable membrane, more specifically, a polymeric porous membrane such as polyethersulfone. The porous membrane 13 has a pore size of up to several tens of nm, and the pore size can be varied to be a lower pore size. The porous membrane 13 gradually releases the taste substance 145 accommodated in the reservoir space 12 from the reservoir space 12 to the outside of the reservoir space 12.

As a mechanism for controlling the gradual release (exudation) of the taste substance 145, for example, at least one of the following two mechanisms can be employed. The first mechanism controls the release by diffusion via small pores of the porous membrane 13. This mechanism controls the amount of the exudation of the taste substance 145 by setting the size of small pores of the porous membrane 13 at a predetermined level. The second mechanism controls the release using the amount of the taste substance 145 exuded from the taste substance impregnated material 14. The exudation amount is determined by adjusting pressure to be applied to the taste substance impregnated material 14, and then the taste substance 145 is caused to reach the top surface 131 of the porous membrane 13 through relatively large pores of the porous membrane 13. In this embodiment, the second mechanism is employed.

The taste substance impregnated material 14 is accommodated within the reservoir space 12. The taste substance 145 is a seasoning such as salt or sugar, is more specifically salt, glutamic acid, inosinic acid, sucrose or the like, and is salt in this embodiment. The molecular sizes of these examples of the taste substance 145 are of the orders of 0.1 nm to 10 nm. As the taste substance impregnated material 14, polymers including agar, hydrogel such as alginic acid, polyurethane, and silicone rubber are used, for example, and such taste substance impregnated material 14 is impregnated with and thus composed of the taste substance 145. In this embodiment, the material 14 is composed of agar impregnated with the taste substance 145. The release of the taste substance 145, with which the taste substance impregnated material 14 is impregnated, from the reservoir space 12 to the outside of the reservoir space 12 is limited by the porous material membrane. The taste substance 145 is released from the reservoir space 12 to the outside of the reservoir space 12, and then is brought into contact with a part of the taste receptors 2010 of a user of the taste substance-supplying article 1, so as to generate the taste for the user of the taste substance-supplying article 1.

The pair of bridge parts 81 is composed of a pair of wires that extend into substantially a horizontal direction in a positional relationship wherein the wires are placed away from each other at substantially equal intervals. As shown in FIG. 1, the right end as one end of the left bridge part 81 is fixed to the left side wall of the reservoir body 112 of the reservoir 11 (see FIG. 2). The left end as one end of the right bridge part 81 is fixed to the right side wall of the reservoir body 112 of the reservoir 11 (see FIG. 2). At the left end as the other end of the left bridge part 81, a pair of wires is integrally connected. Similarly, at the right end as the other end of the right bridge part 81, a pair of wires is integrally connected.

Therefore, the taste substance reservoir part 10 is fixed to the central part of the reservoir part-supporting part 80 composed of the pair of bridge parts 81 of the left bridge part 81 and the right bridge parts 81. As shown in FIG. 1, one end (the left end of the left bridge part 81) of the reservoir part-supporting part 80 composed of the pair of bridge parts 81 is fixed to a part of the oral cavity; that is, a tooth on the left side of the upper jaw of the user of the taste substance-supplying article 1. Moreover, the other end (the right end of the right bridge part 81) of the reservoir part-supporting part 80 composed of the pair of the bridge parts 81 is fixed to a portion other than the part of the oral cavity; that is, a tooth on the right side of the upper jaw of the user of the taste substance-supplying article 1. The pair of bridge parts 81 are fixed in this manner, so that the parts 81 are supported by teeth forming a part of the oral cavity, and the taste substance reservoir part 10 is supported in the oral cavity such that the porous membrane 13 as a taste-releasing part can be brought into contact with a portion of an area being a part of palate 2 and having taste receptors 2010. This support causes the porous membrane 13 as a taste-releasing part to come into contact with the taste receptors 2010, and supplies and causes salt as the taste substance 145 into contact with the taste receptors 2010.

Operation by which the taste substance 145 is released from the taste substance-supplying article 1 according to the above configuration is as described below. First, as shown in FIG. 1, the pair of bridge parts 81 of the taste substance-supplying article 1 are fixed to teeth, respectively, of the upper jaw of the user of the taste substance-supplying article 1. As shown in FIG. 4, this fixation causes the top surface 131 (see FIG. 2) of the porous membrane 13 to come into contact with a portion of an area having taste receptors 2010 of the oral cavity.

Next, the user of the taste substance-supplying article 1 starts a meal by taking a food or drink with an extremely low salt content, such as a salt-free rice ball, into the mouth. At this time, the user of the taste substance-supplying article 1, as shown in FIG. 4, presses the reservoir 11 from the bottom with tongue 6. Therefore, the reservoir body 112 (see FIG. 2) is deformed to change the capacity of the reservoir space 12, thereby lowering the capacity. Specifically, the taste substance impregnated material 14 is squashed, salt that is the taste substance 145 with which the taste substance impregnated material 14 is impregnated is supplied, as indicated with black arrows, through the porous membrane 13, from the bottom surface 132 to the top surface 131 of the porous membrane 13, to the taste receptors 2010 of palate 2, so as to be brought into contact with the taste receptors 2010.

Actually, salt that is the taste substance 145 that is brought into contact with the taste receptors 2010 is in the form of electrolyte dissolved in a solvent such as saliva. The concentration of salt that is brought into contact with the taste receptors 2010 ranges from about 0.01% to 3%. In this embodiment, a patient who undergoes dialysis is assumed to be a user of the taste substance-supplying article 1, the concentration to be employed herein is set at a level as low as possible. As a result, the user of the taste substance-supplying article 1 can sufficiently sense a salty taste of an extremely small amount of salt that is the taste substance 145 from the taste substance-supplying article 1, although the user eats the rice ball having no saltiness. Specifically, the user of the taste substance-supplying article 1 can enjoy the taste of a salt-rich rice ball in a pseudo manner.

With the taste substance-supplying article 1 according to embodiments with the above configurations, the following effects can be obtained. As described above, the taste substance-supplying article 1 is provided with: a taste substance-supplying body having the taste substance 145 that is brought into contact with the taste receptors 2010 to generate a sense of taste, and the porous membrane 13 as a taste-releasing part for retaining the taste substance 145 and gradually releasing the taste substance 145; and the reservoir part-supporting part 80 as a fixing part that fixes the taste substance-supplying body to the oral cavity, so that the taste-releasing part can be brought into contact with a portion of an area being a part of the oral cavity and having the taste receptors 2010. The porous membrane 13 as the taste-releasing part is brought into contact with the taste receptors 2010, and then the taste substance-supplying article 1 supplies and causes the taste substance 145 to come into contact with the taste receptors 2010.

The taste substance-supplying article 1 is provided with a taste substance reservoir part having the reservoir space 12 that can accommodate the taste substance 145 and the porous membrane 13 as a taste-releasing part, wherein the porous membrane 13 gradually releases the taste substance 145 accommodated within the reservoir space 12 from the reservoir space 12 to the outside of the reservoir space 12, the fixing part is supported by a part of the oral cavity, and is provided with the reservoir part-supporting part 80 that supports the taste substance reservoir part 10 in the oral cavity, so that the taste-releasing part can be brought into contact with the taste receptors 2010 in the oral cavity.

With this configuration, when a user takes a food or drink containing almost no taste substance 145 such as salt into the oral cavity at mealtime, a little amount of the taste substance 145 such as salt can be supplied to the taste receptors 2010. Accordingly, the user of the taste substance-supplying article 1 can sense a synthesized taste of the taste of a food or drink containing almost no taste substance 145 such as salt and the taste of the taste substance 145 such as salt supplied to the taste receptors 2010. At this time, the taste substance 145 is directly supplied to and is brought into contact with the taste receptors 2010, the user of the taste substance-supplying article 1 can sense richly the taste of even a little amount of the taste substance 145. As a result, a food or drink containing almost no taste substance 145 such as salt and an extremely little amount of the taste substance 145 such as salt coming from the taste substance-supplying article 1 enable the user to enjoy, in a pseudo manner, the taste of a food or drink containing a large amount of the taste substance 145. Hence, for example, when a person under a dietary salt restriction, such as a patient who undergoes dialysis, eats a rice ball with no saltiness, the taste substance 145 such as salt is efficiently supplied from the taste substance-supplying article 1 to the taste receptors 2010 without waste, although the rice ball itself has no salty taste. As a result, with even an extremely little amount of the taste substance 145, a user of the taste substance-supplying article 1 can sense the palatability of a rice ball with a clear salty taste, and thus the quality of life is improved through such meals.

Moreover, the taste substance reservoir part 10 has the reservoir 11 having an opening, the reservoir space 12 is composed of the internal space of the reservoir 11, and the porous membrane 13 as a taste-releasing part is disposed at the opening so as to cover the opening of the opening part 111.

With this configuration, the taste substance 145 can be accommodated within the reservoir 11 when the taste substance-supplying article 1 is not used. In addition, the taste substance 145 can be released from the reservoir 11 to the outside of the reservoir 11 via the opening.

Moreover, the taste-releasing part is composed of the porous membrane 13. This configuration can facilitate the gradual release of the taste substance 145 from the reservoir space 12 to the outside of the reservoir space 12 through the porous membrane 13.

Furthermore, the reservoir 11 is deformable so that the capacity of the reservoir space 12 can be varied. With this configuration, the taste substance 145 can be easily released from the reservoir space 12 to the outside of the reservoir space 12 by changing the capacity of the reservoir space 12 of the reservoir 11.

Furthermore, the taste substance reservoir part 10 is fixed to the bridge parts 81 at the central part of the reservoir part-supporting part 80; that is, between the pair of bridge parts 81, wherein the one end of the reservoir part-supporting part 80 is fixed to a tooth, as a part of the oral cavity, on the left side of the upper jaw, and the other end of the reservoir part-supporting part 80 is fixed to a tooth, as another part other than the part of the oral cavity, on the right side of the upper jaw. With this configuration, the reservoir part-supporting part 80 composed of the pair of bridge parts 81 can be easily supported by teeth forming a part of the oral cavity, thereby easily causing the porous membrane 13 as the taste-releasing part of the taste substance reservoir part 10 to come into contact with the taste receptors 2010.

Figure 5:
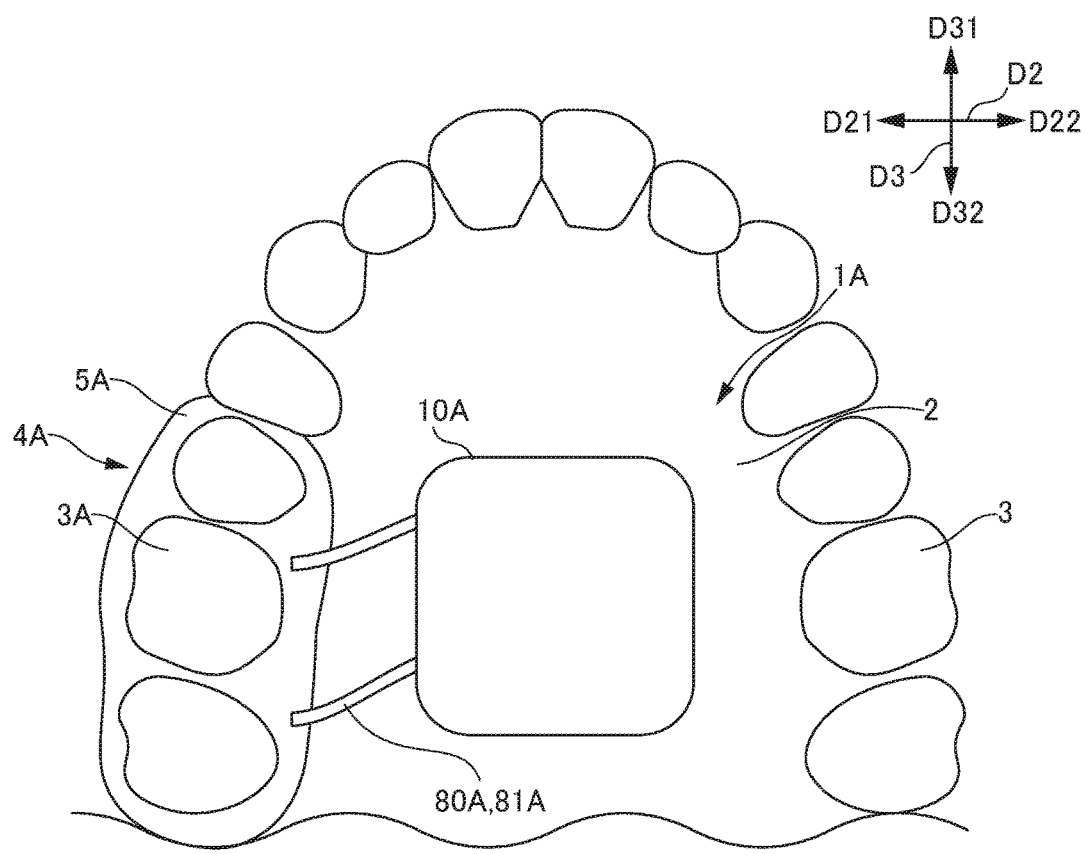
FIG. 5 is a schematic view showing how a reservoir part-supporting part 80A of a taste substance-supplying article 1A according to a $2^{nd}$ embodiment of the present invention is fixed to false teeth 4A.

Next, a taste substance-supplying article 1A according to the $2^{nd}$ embodiment will be explained referring to FIG. 5. FIG. 5 is a schematic view showing how a reservoir part-supporting part 80A of the taste substance-supplying article 1A according to the $2^{nd}$ embodiment of the present invention is fixed to false teeth 4A.

In the taste substance-supplying article 1A according to the $2^{nd}$ embodiment, the configuration of the reservoir part-supporting part 80A differs from that of the reservoir part-supporting part 80 in the $1^{st}$ embodiment. Configurations other than this are the same as those in the $1^{st}$ embodiment, and thus explanation for the same members is omitted.

A bridge part 81A composing the reservoir part-supporting part 80A is composed of a pair of wires extending substantially a horizontal direction while being spaced apart at substantially equal intervals. As shown in FIG. 5, the right end as one end of the bridge part 81A is fixed to the left side wall of the reservoir body 112 of the reservoir 11 (see FIG. 2) of the taste substance reservoir part 10A. At the left end as the other end of the bridge part 81A, a pair of wires are connected and fixed not to a denture 3A of false teeth 4A fixed to the upper jaw as an attachment member to be fixed to a part of the oral cavity, but to a false tooth body 5A.

As a result of such fixation, the bridge part 81A is fixed to and supported by the false teeth 4A as attachment members, the taste substance reservoir part 10A is supported in the oral cavity, so that the porous membrane 13 as a taste-releasing part can be brought into contact with a portion of an area being a part of palate 2 and having the taste receptors 2010 (see FIG. 4). With such support, the porous membrane 13 as the taste-releasing part is brought into contact with the taste receptors 2010, so as to supply and causes salt as the taste substance 145 (see FIG. 4) to come into contact with the taste receptors 2010.

With the taste substance-supplying article 1A according to the $2^{nd}$ embodiment, the following effects can be obtained. The taste substance reservoir part 10A is fixed to one end of the reservoir part-supporting part 80A, and the other end of the reservoir part-supporting part 80A is fixed to an attachment member to be fixed to a part of the oral cavity. The attachment member is composed of false teeth 4A fixed to the upper jaw, and the porous membrane 13 as a taste-releasing part is brought into contact with the taste receptors 2010 of palate 2.

With this configuration, a user wears false teeth 4A at mealtime, so that the porous membrane 13 as a taste-releasing part of the taste substance-supplying article 1A can be caused to come into contact with the taste receptors 2010 of the palate 2. Therefore, a step required separately for disposing the taste substance-supplying article 1A within the oral cavity, in addition to a step of disposing the false teeth 4A can be saved. In addition, after a meal, the care of the false teeth 4A and the care of the taste substance-supplying article 1A can be performed simultaneously. In addition, false teeth 4A are fixed firmly to the palate 2, so that the porous membrane 13 as the taste-releasing part can be stably kept in close contact with the taste receptors 2010 of the palate 2.

Figure 6:
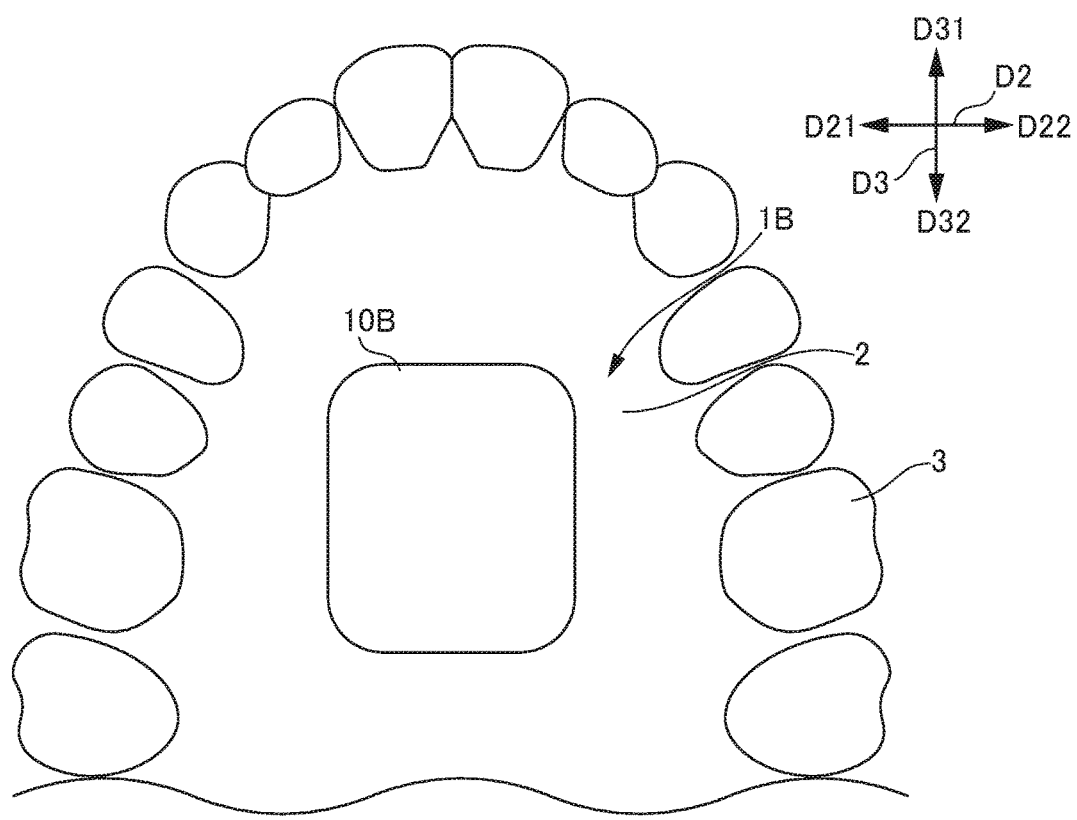
FIG. 6 is a schematic exploded perspective view showing how a taste substance-supplying article 1B according to a $3^{rd}$ embodiment of the present invention is fixed to palate 2.

Next, a taste substance-supplying article 1B according to the $3^{rd}$ embodiment will be explained referring to FIG. 6. FIG. 6 is a schematic exploded perspective view showing how the taste substance-supplying article 1B according to the $3^{rd}$ embodiment of the present invention is fixed to palate 2.

In the taste substance-supplying article 1B according to the $3^{rd}$ embodiment, the configuration of the reservoir part-supporting part differs from that of the reservoir part-supporting part 80 in the $1^{st}$ embodiment. Configurations other than this are the same as those in the $1^{st}$ embodiment, and thus explanation for the same members is omitted.

The reservoir part-supporting part is composed of the porous membrane 13 having a cohesive top surface 131 (see FIG. 2). As the porous membrane 13 having the cohesive top surface 131, for example, the porous membrane 13 coated with a false tooth stabilizer (e.g., Shionogi & Co., Ltd. Touch Collect II (registered trademark) (containing polyethylene glycol (PEG) and carmellose sodium) and Eisai Sea Bond (registered trademark) (containing polyethylene glycol (PEG) and sodium alginate)) can be used. Before a user of the taste substance-supplying article 1B has a meal, the porous membrane 13 having the cohesive top surface 131 is bonded to a portion of an area being a part of the palate 2 and having taste receptors 2010. Accordingly, the taste substance-supplying article 1B having the taste substance reservoir part 10B is fixed to and supported by the palate 2.

With the taste substance-supplying article 1B according to the $3^{rd}$ embodiment, the following effects can be obtained. The reservoir part-supporting part 80B is composed of the cohesive porous membrane 13, and the porous membrane 13 can be easily bonded to a portion of the palate 2 of the user of the taste substance-supplying article 1B; that is a portion where taste receptors 2010 are present. Therefore, a step of wearing the taste substance-supplying article 1B before meal can be drastically saved.

Figure 7:
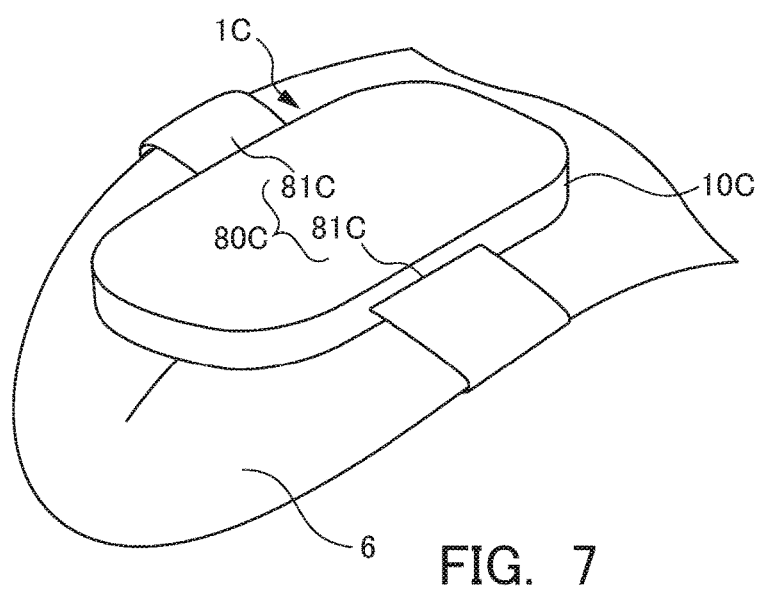
FIG. 7 is a schematic exploded perspective view showing how a taste substance-supplying article 1C according to a $4^{th}$ embodiment of the present invention is fixed to tongue 6.

Next, a taste substance-supplying article 1C according to the $4^{th}$ embodiment will be explained referring to FIG. 7. FIG. 7 is a schematic exploded perspective view showing how the taste substance-supplying article 1C according to the $4^{th}$ embodiment of the present invention is fixed to tongue 6.

In the taste substance-supplying article 1C according to the $4^{th}$ embodiment, the configuration of the reservoir part-supporting part 80C differs from that of the reservoir part-supporting part 80 in the $1^{st}$ embodiment. Accordingly, the part of the oral cavity with which the porous membrane 13 is brought into contact differs from palate 2 that is a part of the oral cavity with which the porous membrane 13 is brought into contact in the $1^{st}$ embodiment. Configurations other than this are the same as those in the $1^{st}$ embodiment, and thus explanation for the same members is omitted.

The reservoir part-supporting part 80C has a band-shaped part 81C. The band-shaped part 81C is strip-shaped. The band-shaped part 81C is rolled to form a ring, wherein one end of the band-shaped part 81C is fixed to the left side wall of the reservoir body 112 of the reservoir 11 (see FIG. 2) of the taste substance-supplying article 1C. The other end of the band-shaped part 81C is fixed to the right side wall of the reservoir body 112 of the reservoir 11 (see FIG. 2) of the taste substance-supplying article 1C. Therefore, the taste substance reservoir part 10C of the taste substance-supplying article 1C is fixed to the central part of the reservoir part-supporting part 80C composed of the band-shaped part 81C.

As shown in FIG. 7, the reservoir part-supporting part 80C and the taste substance reservoir part 10C are fixed to tongue 6, so that the reservoir part-supporting part 80C and the taste substance reservoir part 10C wrap around the tongue 6. At this time, the top surface 131 of the porous membrane 13 (see FIG. 2) as a taste-releasing part is brought into contact with a part of the taste receptors 2010 on the top surface of the tongue 6.

With the taste substance-supplying article 1C according to the $4^{th}$ embodiment, the following effects can be obtained. The reservoir part-supporting part 80C is a cyclic portion having one end and the other end, wherein the taste substance reservoir part 10C is fixed to the central part of the reservoir part-supporting part 80C, the reservoir part-supporting part 80C and the taste substance reservoir part 10C are fixed to tongue 6, so that the reservoir part-supporting part 80C and the taste substance reservoir part 10C wrap around the tongue 6, and the porous membrane 13 as a taste-releasing part is brought into contact with the taste receptors 2010 on the top surface of the tongue 6.

With this configuration, before a user of the taste substance-supplying article 1C has a meal, the taste substance-supplying article 1C can be easily placed and fixed to the tongue 6 that is a part of the oral cavity, and thus the reservoir part-supporting part 80C and the taste substance reservoir part 10C can be supported by the tongue 6.

Figure 8:
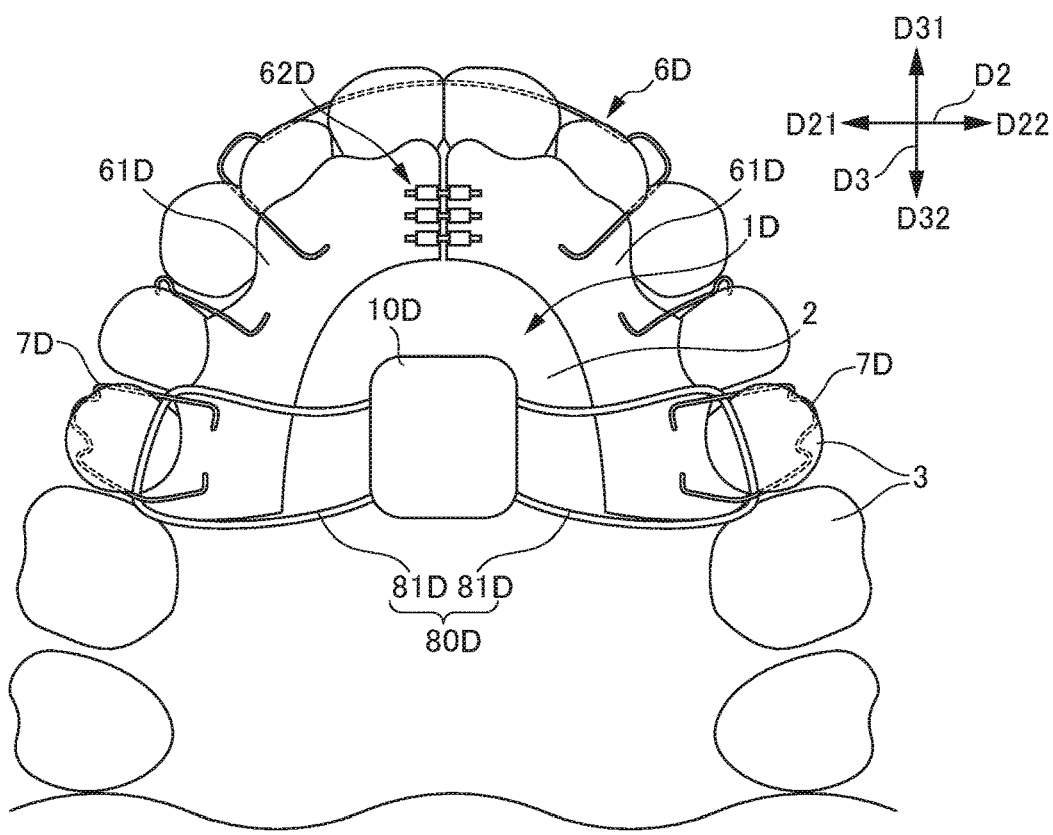
FIG. 8 is a schematic view showing how a reservoir part-supporting part 80D of a taste substance-supplying article 1D according to a $5^{th}$ embodiment of the present invention is fixed to a dental brace 6D.

Next, a taste substance-supplying article 1D according to the 5$^{th}$ embodiment will be explained referring to FIG. 8. FIG. 8 is a schematic view showing how a reservoir part-supporting part 80D of a taste substance-supplying article 1D according to the 5$^{th}$ embodiment of the present invention is fixed to a dental brace 6D.

In the taste substance-supplying article 1D according to the 5$^{th}$ embodiment, an object to which one end of the reservoir part-supporting part 80D is fixed differs from the object to which one end of the reservoir part-supporting part 80D in the 1$^{st}$ embodiment is fixed. Accordingly, the configuration of the bridge part 81D composing the reservoir part-supporting part differs from that of the bridge part 81D in the 1$^{st}$ embodiment. Configurations other than this are the same as those in the 1$^{st}$ embodiment, and thus explanation for the same members is omitted.

The dental brace 6D is provided with a pair of instrument bodies 61D, a body-connecting member 62D, and a wire part 7D fixed to the instrument bodies 61D. The instrument bodies 61D are made of resin and connected with the metallic body-connecting member 62D. The body-connecting member 62D has a rotating part that is rotated by the insertion of a tip of a thin object such as a wire tip, and is composed to be able to adjust the distance between a pair of the instrument bodies 61D in the horizontal direction D2 by rotating the rotating part. The wire part 7D is hooked on and fixed to teeth 3, so that the dental brace 6D is fixed to the teeth 3.

The bridge part 81D is composed of an elastic flexible linear material, and is composed of linear rubber in this embodiment. The left bridge part 81D is hooked on the left wire part 7D of the dental brace 6D to be fixed to the upper jaw, as an attachment member to be fixed to a part of the oral cavity, so that the left bridge part 81D is supported and fixed. The right bridge part 81D is hooked on the right wire part 7D of the dental brace 6D to be fixed to the upper jaw, so that the right bridge part 81D is supported and fixed. When the bridge part 81D is hooked on the right wire part 7D of the dental brace 6D, the bridge part 81D is temporarily stretched elastically, so as to hook it on the wire part 7D.

Specifically, the taste substance reservoir part 10D is fixed to the central part of the reservoir part-supporting part 80D composed of the pair of bridge parts 81D. The left end of the left bridge part 81D as one end of the reservoir part-supporting part 80D is fixed to the left portion of the dental brace 6D as an attachment member to be fixed to a part of the oral cavity. The right end of the right bridge part 81D as the other end of the reservoir part-supporting part 80D is fixed to the right portion of the dental brace 6D as an attachment member to be fixed to a portion other than the part of the oral cavity.

With the taste substance-supplying article 1D according to the 5$^{th}$ embodiment, the following effects can be obtained. The attachment member is composed of the dental brace 6D to be fixed to the upper jaw, and the porous membrane 13 as a taste-releasing part is brought into contact with a portion of an area being a part of the palate 2 and having the taste receptors 2010. With this configuration, the taste substance-supplying article 1D is fixed to the dental brace 6D that is firmly fixed to the palate 2, so that within the oral cavity, the taste substance-supplying article 1D can be stably supported and the contact of the porous membrane 13 as a taste-releasing part with the taste receptors 2010 of the palate 2 can be ensured.

Figure 9:
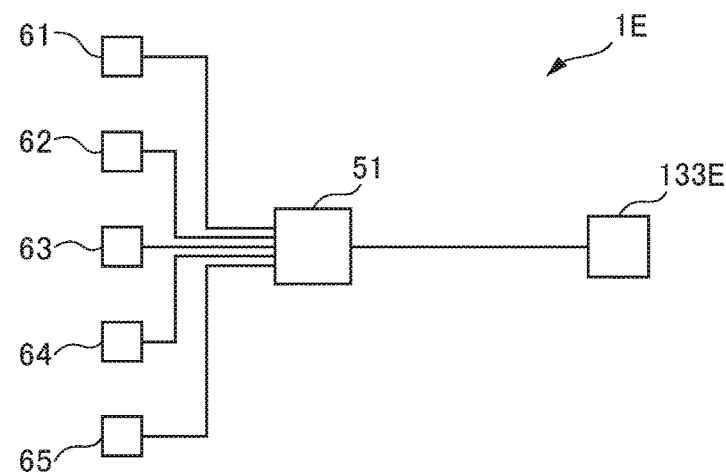
FIG. 9 is a block diagram showing a taste substance-supplying article 1E according to a $6^{th}$ embodiment of the present invention.
Figure 10:
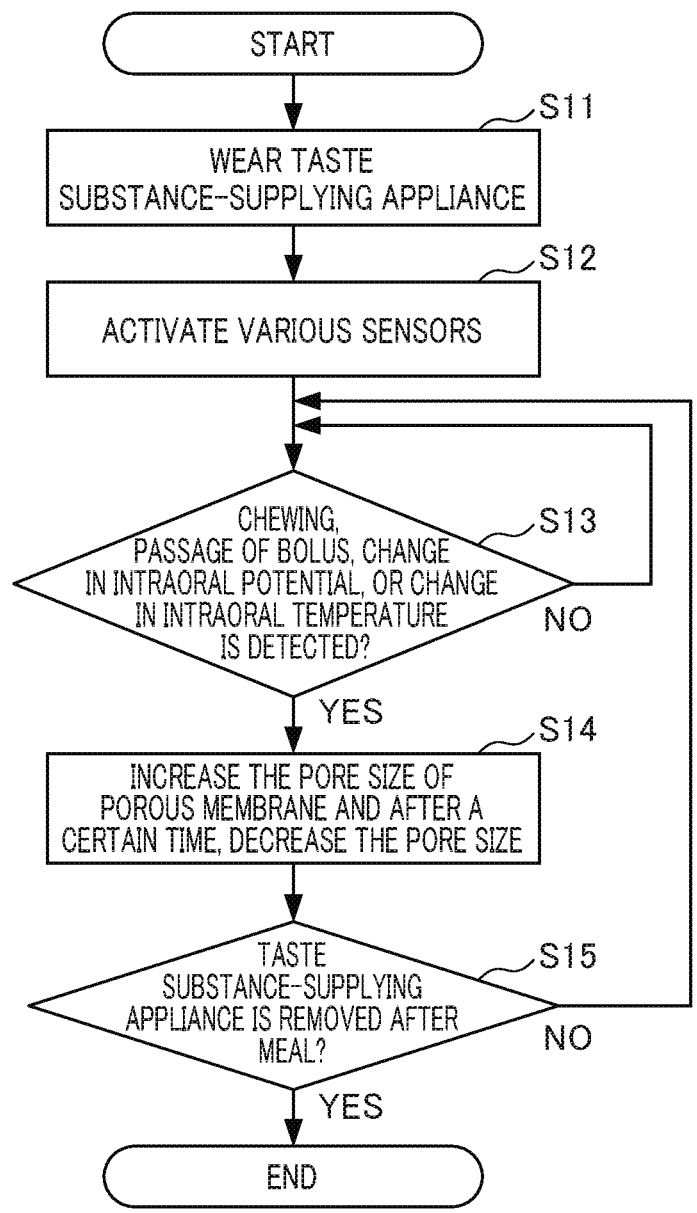
FIG. 10 is a flow chart showing the control of a taste substance-supplying article 1E according to the $6^{th}$ embodiment of the present invention by a control part 51.

Next, a taste substance-supplying article 1E according to the 6$^{th}$ embodiment will be explained referring to FIG. 9 and FIG. 10. FIG. 9 is a block diagram showing the taste substance-supplying article 1E according to the 5$^{th}$ embodiment of the present invention. FIG. 10 is a flow chart showing the control performed by a control part 51 of the taste substance-supplying article 1E according to the 5$^{th}$ embodiment of the present invention.

The taste substance-supplying article 1E according to the 6$^{th}$ embodiment differs from the taste substance-supplying article 1 according to the 1$^{st}$ embodiment in that the control part 51 controls to cause the automatic release of a taste substance such as salt from the porous membrane 13. Configurations other than this are the same as those in the 1$^{st}$ embodiment, and thus explanation for the same members is omitted.

As shown in FIG. 9, the taste substance-supplying article 1E has a small control part 51 within the article, an actuator 133E as a taste releasing part-changing drive part, an acceleration sensor 61, a vibration sensor 62, a voltage sensor 63 and a temperature sensor 64 as a food or drink-detecting part, and a wearing sensor 65 within the article.

The acceleration sensor 61 detects the acceleration generated when a user of the taste substance-supplying article 1E chews/drinks a food or drink. The vibration sensor 62 detects the vibration resulting from the collision of a food or drink taken into the oral cavity of a user of the taste substance-supplying article 1E with the taste substance-supplying article 1E. The voltage sensor 63 detects a change in intraoral potential resulting from the intake of a food or drink into the oral cavity of a user of the taste substance-supplying article 1E. The temperature sensor 64 detects a change in intraoral temperature resulting from the intake of a food or drink into the oral cavity of a user of the taste substance-supplying article 1E. Specifically, the acceleration sensor 61, the vibration sensor 62, the voltage sensor 63, and, the temperature sensor 64 can all detect the intake of a food or drink into the oral cavity of a user of the taste substance-supplying article 1E.

The wearing sensor 65 is provided with a piezoelectric element, and detects the deformation of the reservoir 11 due to force applied to the taste substance-supplying article 1E through the bridge parts 81. The actuator 133E is self-contained in the porous membrane 13, and is controlled by the control part 51 to increase or decrease the pore size of the porous membrane 13. Specifically, a mechanism to be used as a mechanism for controlling the gradual release (exudation) of the taste substance 145 from the porous membrane 13 in this embodiment involves driving the actuator 133E to change; that is, to increase or decrease the pore size of the porous membrane 13 within a range of 1 nm-10 nm, thereby gradually releasing the taste substance 145 accommodated within the reservoir space 12 from the taste-releasing part.

The control part 51 has a processor (not shown) for performing various types of arithmetic processing, a memory (not shown) for storing various types of information, and a power supply part (not shown) composed of a battery for supplying electric power to them, for example. The control part 51 is electrically connected to the actuator 133E, the acceleration sensor 61, the vibration sensor 62, the voltage sensor 63, the temperature sensor 64, and the wearing sensor 65. The control part 51 drives the actuator 133E based on signals from the acceleration sensor 61, the vibration sensor 62, the voltage sensor 63, the temperature sensor 64, and, the wearing sensor 65.

Hereafter, the control performed by the control part 51 when a user of the taste substance-supplying article 1E takes a food or drink into the oral cavity is explained based on FIG. 10. First, in step S11, a pair of bridge parts 81 (see FIG. 1) of the taste substance-supplying article 1E is fixed to teeth of the upper jaw of the user of the taste substance-supplying article 1E, and the taste substance-supplying article 1E is fixed to palate 2 of the user of the taste substance-supplying article 1E. As a result, force is applied to the wearing sensor 65 of the taste substance-supplying article 1E through the bridge parts 81, and then the wearing sensor 65 detects that the taste substance-supplying article 1E is fixed to the palate 2. Accordingly, in step S12, the control part 51 controls to activate the acceleration sensor 61, the vibration sensor 62, the voltage sensor 63, and, the temperature sensor 64.

Next, the control part 51, in step 13, determines whether or not at least one of the acceleration sensor 61, the vibration sensor 62, the voltage sensor 63, and the temperature sensor 64 detects the intake of a food or drink into the oral cavity of a user of the taste substance-supplying article 1E. In step 13, when the sensor detects (YES) the intake of a food or drink into the oral cavity of the user of the taste substance-supplying article 1E, the operation by the control part 51 proceeds to step 14. In step 13, when the sensor does not detect (NO) the intake of a food or drink into the oral cavity of the user of the taste substance-supplying article 1E, the operation by the control part 51 goes back to step 13.

In step 14, the control part 51 controls the actuator 133E to initiate the release of the taste substance 145 accommodated within the reservoir space 12 from the reservoir space 12 to the outside of the reservoir space 12. Specifically, the actuator 133E appropriately increases the pore size of the porous membrane 13, so as to supply and cause the taste substance 145 into contact with taste receptors 2010 of the palate 2 through pores of the porous membrane 13. After the elapse of a certain period of time, the control part 51 controls the actuator 133E to decrease the pore size of the porous membrane 13. Therefore, the release of the taste substance 145 accommodated within the reservoir space 12 from the reservoir space 12 to the outside of the reservoir space 12 is stopped.

Next, the control part 51 determines, in step 15, whether or not the taste substance-supplying article 1E is removed from the palate 2 of the user of the taste substance-supplying article 1E after meal based on signals from the wearing sensor 65. In step 15, when the taste substance-supplying article 1E is removed (YES) from the palate 2 of the user of the taste substance-supplying article 1E, the control part 51 terminates the operation. In step 15, when the taste substance-supplying article 1E is not removed (NO) from the palate 2 of the user of the taste substance-supplying article 1E, the operation by the control part 51 goes back to step 13.

With the taste substance-supplying article 1E according to the $6^{th}$ embodiment, the following effects can be obtained. The taste substance-supplying article 1E is provided with: the actuator 133E as a taste releasing part-changing drive part for changing the porous membrane 13, so as to gradually release the taste substance 145 accommodated within the reservoir space 12 from the porous membrane 13 as a taste-releasing part; the acceleration sensor 61, the vibration sensor 62, the voltage sensor 63, and the temperature sensor 64 as a food or drink-detecting part that can detect the intake of a food or drink into the oral cavity of a user of the taste substance-supplying article 1E by detecting at least one of the chewing by the user of the taste substance-supplying article 1E, the intake of a food or drink into the oral cavity of the user of the taste substance-supplying article 1E, an potential change in the oral cavity of the user of the taste substance-supplying article 1E, and a change in intraoral temperature of the user of the taste substance-supplying article 1E; and the control part 51 that controls the actuator 133E as the taste releasing part-changing drive part to initiate the release of the taste substance 145 accommodated within the reservoir space 12 from the reservoir space 12 to the outside of the reservoir space 12, when the food or drink-detecting part detects the intake of a food or drink into the oral cavity of the user of the taste substance-supplying article 1E.

With this configuration, the taste substance-supplying article 1E can automatically release the taste substance 145 to the taste receptors 2010, so that the use of tongue 6 is not required to release the taste substance 145, unlike the taste substance-supplying article 1 in the $1^{st}$ embodiment. Hence, a user can enjoy the taste coming from the taste substance 145 without straining the tongue 6. In addition, the amount of the taste substance 145 to be released can be controlled accurately.

Figure 11:
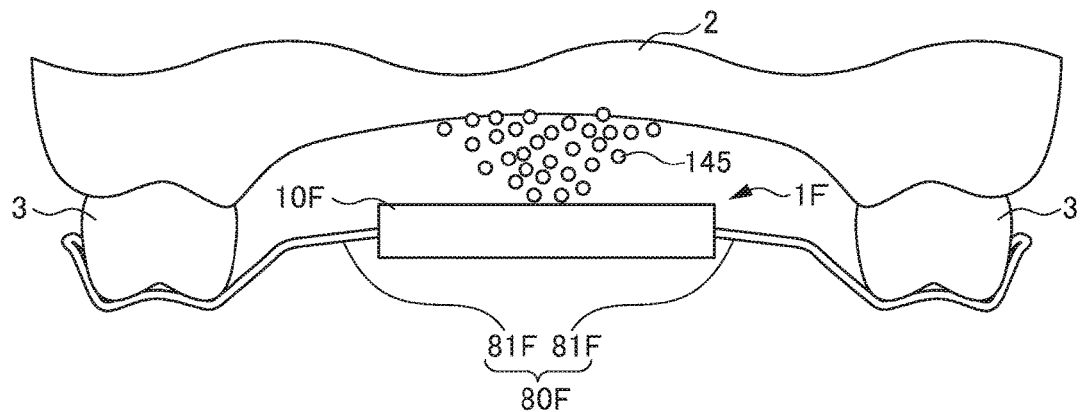
FIG. 11 is a schematic front view showing how a taste substance-supplying article 1F according to a $7^{th}$ embodiment of the present invention is fixed to teeth 3 of the upper jaw.

Next, a taste substance-supplying article 1F according to the $7^{th}$ embodiment will be explained referring to FIG. 11. FIG. 11 is a schematic front view showing how the taste substance-supplying article 1F according to the $7^{th}$ embodiment of the present invention is fixed to teeth 3 of the upper jaw.

In the taste substance-supplying article 1F according to the $7^{th}$ embodiment, the configuration of the reservoir part-supporting part 80F differs from that of the reservoir part-supporting part 80 in the $6^{th}$ embodiment. In addition, the configuration of the taste-releasing part of the taste substance-supplying article 1E differs from that of the taste-releasing part of the taste substance-supplying article 1E in the $6^{th}$ embodiment. Configurations other than this are the same as those in the $6^{th}$ embodiment, and thus explanation for the same members is omitted.

The pair of bridge parts 81F composing the reservoir part-supporting part 80F is supported by teeth 3 forming a part of the oral cavity, however, the taste substance reservoir part 10F is not brought into contact with palate 2 as shown in FIG. 11. The taste-releasing part of the reservoir part-supporting part 80F is disposed away from the palate 2 in a positional relationship such that it faces the palate 2.

In the taste-releasing part of the taste substance-supplying article 1E in the $6^{th}$ embodiment, the actuator 133E is driven to appropriately increase the pore size of the porous membrane 13. However, in the taste substance-supplying article 1F in the $7^{th}$ embodiment, the actuator is composed of a piezoelectric material (piezoelectric vibrator) for generating surface acoustic wave (SAW), and composes a SAW device (surface acoustic wave device). The piezoelectric material is driven to atomize a liquid taste substance 145 existing at and in the vicinity of the pores of the porous membrane 13, so as to be brought into contact with a portion of an area being a part of the palate 2 and having taste receptors. Accordingly, the taste substance 145 is supplied from the taste-releasing part to the taste receptors.

Figure 12:
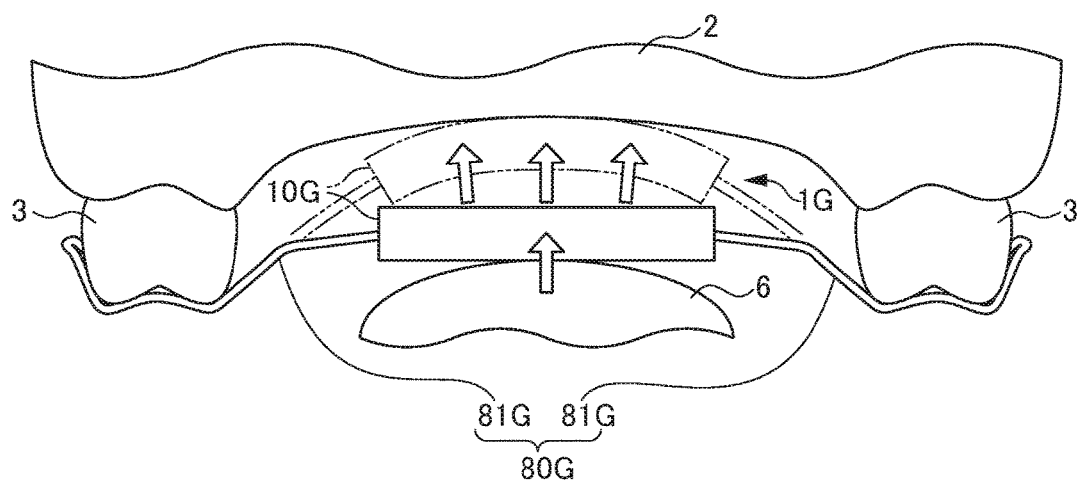
FIG. 12 is a schematic front view showing how a taste substance-supplying article 1G according to an $8^{th}$ embodiment of the present invention is fixed to teeth 3 of the upper jaw.

Next, a taste substance-supplying article 1G according to the $8^{th}$ embodiment will be explained referring to FIG. 12. FIG. 12 is a schematic front view showing how the taste substance-supplying article 1G according to the $8^{th}$ embodiment of the present invention is fixed to teeth 3 of the upper jaw.

In the taste substance-supplying article 1G according to the $8^{th}$ embodiment, the configuration of the pair of bridge parts 81G composing the reservoir part-supporting part 80G differs from that of the pair of bridge parts 81 composing the reservoir part-supporting part 80 in the $1^{st}$ embodiment.

Configurations other than this are the same as those in the 1st embodiment, explanation for the same members is omitted.

The pair of bridge parts 81G composing the reservoir part-supporting part 80G are composed using a material such as flexible and elastic rubber or spring, and rubber is used in this embodiment. The pair of bridge parts 81G is supported by teeth 3 forming a part of the oral cavity. The taste substance reservoir part 10G is, as shown in FIG. 12, not brought into contact with palate 2. The taste-releasing part of the reservoir part-supporting part 80G is disposed away from the palate 2 in a positional relationship such that it faces the palate 2.

For example, when the reservoir part-supporting part 80G of the taste substance-supplying article 1G is pressed with tongue 6, the taste substance reservoir part 10G is deformed by the elasticity of flexible rubber, and then the taste-releasing part is brought into contact with taste receptors. Accordingly, the taste substance 145 is supplied from the taste-releasing part to taste receptors.

Figure 13:
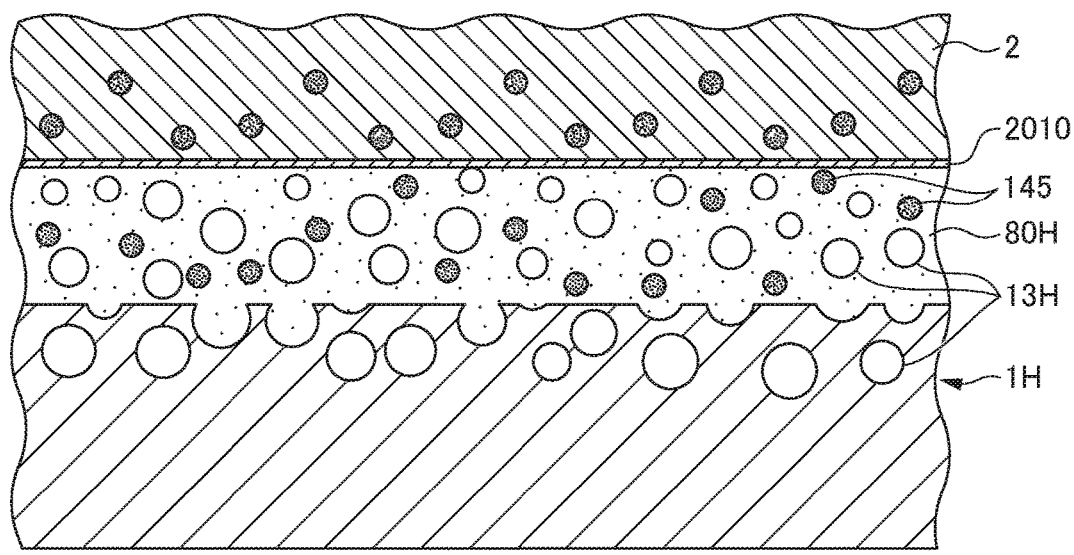
FIG. 13 is a schematic sectional view showing how taste-releasing parts 13H of a taste substance-supplying article 1H according to a $9^{th}$ embodiment of the present invention are dissolved.

Next, a taste substance-supplying article 1H according to the 9th embodiment will be explained referring to FIG. 13. FIG. 13 is a schematic sectional view showing how taste-releasing parts 13H of the taste substance-supplying article 1H according to the 9th embodiment of the present invention are dissolved.

The fixing part and the taste-releasing parts in the taste substance-supplying article 1H according to the 9th embodiment differ from those in the 1st embodiment in that: the fixing part for fixing the taste substance-supplying body to the oral cavity is composed of a cohesive substance; and the taste-releasing parts can be dissolved in the oral cavity. Configurations other than this are the same as those in the 1st embodiment, and thus explanation for the same members is omitted.

The taste-releasing parts 13H are composed of a material that is gradually dissolved when the parts are brought into contact with water contained in saliva. Specifically, the taste-releasing parts 13H are composed of polyethylene glycol, for example. As the taste substance 145, sodium chloride, sodium acetate, or the like is used, and the taste substance 145 is solidified in a state of being mixed with polyethylene glycol composing the taste-releasing parts 13H. The amount of the taste substance 145 in the taste substance-supplying article 1H is about 80 mg. The taste substance 145 and the taste-releasing parts 13H having such configurations compose a taste substance-supplying body. The fixing part 80H is composed of a cohesive substance bonded to the top surface of the taste substance-supplying body. As the cohesive substance, for example, a material having proper adhesiveness such as high-polymer polyethylene glycol is used. The top surface of the taste substance-supplying body is fixed to palate 2 while being brought into contact with a part of taste receptors 2010, because of the cohesive substance.

Because of saliva adhering to the palate 2, polyethylene glycol composing the taste-releasing parts 13H is dissolved in the oral cavity. As polyethylene glycol is dissolved, the taste substance 145 composed of sodium chloride, sodium acetate or the like is released from the taste substance-supplying article 1H, passes through the fixing part 80H, and is then supplied to taste receptors 2010. The taste-releasing parts 13H are completely dissolved within several minutes to several hours.

With the taste substance-supplying article 1H according to the 9th embodiment, the following effects can be obtained.

The fixing part 80H is composed of the cohesive substance. With this configuration, the taste substance-supplying article 1H can be easily fixed to the palate 2, for example. In addition, the taste-releasing parts 13H can be dissolved within the oral cavity. This configuration realizes a feature wherein a taste substance reservoir part that is a container for accommodating the taste substance 145 does not remain within the oral cavity, and the sense of use can be improved when a user uses the taste substance-supplying article 1H.

Figure 14:
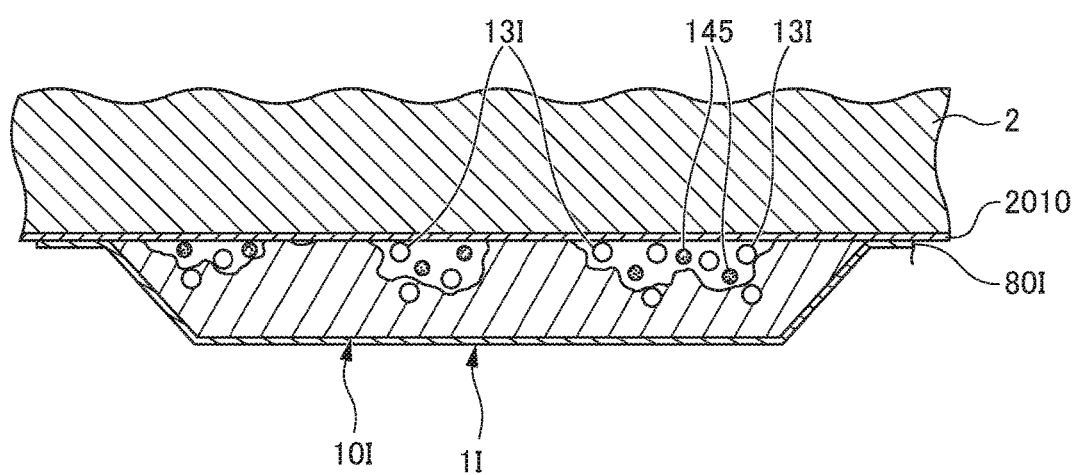
FIG. 14 is a schematic sectional view showing how taste-releasing parts 13I of a taste substance-supplying article 1I according to a tenth embodiment of the present invention are dissolved.

Next, a taste substance-supplying article 1I according to the 10th embodiment will be explained referring to FIG. 14. FIG. 14 is a schematic sectional view showing how taste-releasing parts 13I of the taste substance-supplying article 1I according to the 10th embodiment of the present invention are dissolved.

The taste substance-supplying article 1I according to the 10th embodiment differs from the taste substance-supplying article 1H in the 9th embodiment in that the fixing part for fixing the taste substance-supplying body to the oral cavity fixes the taste substance-supplying body to a part of the oral cavity so as to cover the taste substance-supplying body. Configurations other than this are the same as those in the 1st embodiment, and thus explanation for the same members is omitted.

The taste substance-supplying body 10I composed of the taste-releasing parts 13I composed of the same material as that in the 9th embodiment and the taste substance 145 is covered by a cohesive substance composing the fixing part 80I. One end of the fixing part 80I is fixed to the taste receptors 2010 of the palate 2. Therefore, the taste substance-supplying body 10I is fixed by the fixing part 80I to a part of palate 2.

With the taste substance-supplying article 1I according to the 10th embodiment, the following effects can be obtained.

The taste-releasing parts 13I and the taste substance 145 can be caused to come into direct contact with the taste receptors 2010 without the fixing part 80I, so that water contained in saliva directly adhering to the taste receptors 2010 can accelerate the progress of the dissolution of the taste-releasing parts. As a result, a user can receive the taste instantaneously and can sense instantaneously the taste from the taste substance.

Figure 15:
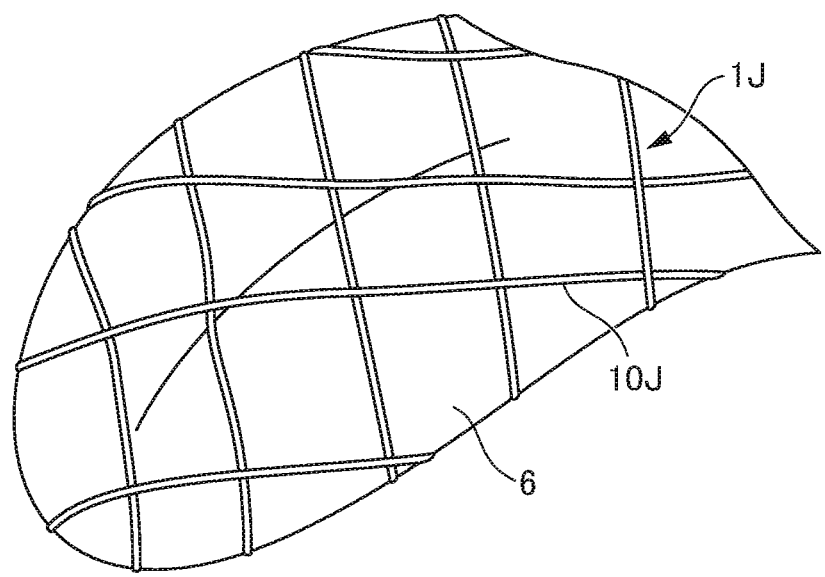
FIG. 15 is a schematic perspective view showing how a taste substance-supplying article 1J according to an eleventh embodiment of the present invention is fixed to tongue 6.

Next, a taste substance-supplying article 1J according to the 11th embodiment will be explained referring to FIG. 15. FIG. 15 is a schematic perspective view showing how the taste substance-supplying article 1J according to the 11th embodiment of the present invention is fixed to tongue 6.

The taste substance-supplying article 1J according to the 11th embodiment differs from the taste substance-supplying article 1H in the 9th embodiment in that the taste substance-supplying article 1J is entirely net-shaped. Configurations other than this are the same as those in the 9th embodiment, and thus explanation for the same members is omitted.

The taste-releasing part and the taste substance composing the taste substance-supplying body 10J are composed of the same materials as those of the taste-releasing parts 13H and the taste substance 145 in the 9th embodiment. Similarly, the fixing part is composed of the same material as that of the fixing part 80H in the 9th embodiment. The taste substance-supplying body 10J is net-shaped, so that the taste substance-supplying body 10J is disposed to cover the tongue 6 surrounding almost the entire tongue 6. A fixing part composed of a cohesive substance is provided on the surface of the taste substance-supplying body 10J, so that the taste substance-supplying body 10J is fixed to the tongue 6.

With the taste substance-supplying article 1J according to the 11th embodiment, the following effects can be obtained.

The taste substance-supplying body 10J is fixed to a part of the tongue 6 that is a part of the oral cavity, so as to cover a portion of an area being a part of the oral cavity and having taste receptors. In addition, the taste substance-supplying body 10J is net-shaped. With this configuration, although the taste substance-supplying body 10J is disposed and fixed covering the tongue 6 so as to almost entirely surround the tongue 6 having taste receptors, taste receptors of the tongue 6 can be partially kept uncovered by the taste substance-supplying body 10J. This can prevent a problem such that the whole taste receptors of a user of the taste substance-supplying article 1J sense only the taste from the taste substance and cannot sense the taste of a food the user actually eats. As a result, a user of the taste substance-supplying article 1J can sense a taste in a balanced way.

Next, a taste substance-supplying article 1K according to the $12^{th}$ embodiment will be explained referring to FIG. 16.

Figure 16:
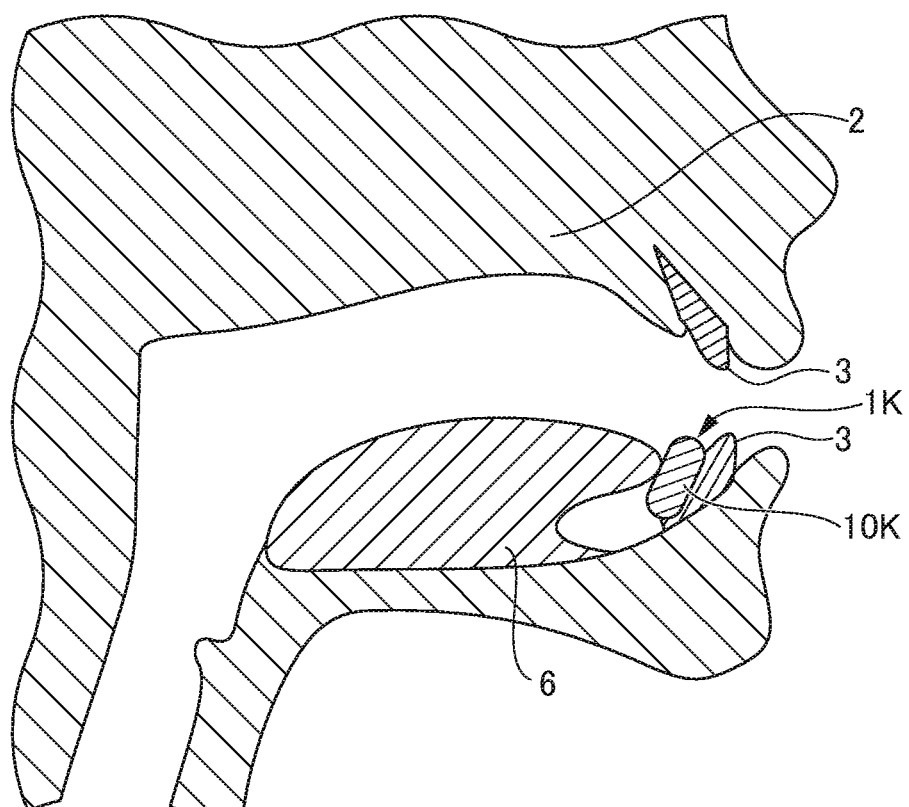
FIG. 16 is a schematic sectional view showing how a taste substance-supplying body 10K of a taste substance-supplying article 1K according to a twelfth embodiment of the present invention is in contact with tongue 6.

FIG. 16 is a schematic sectional view showing how the taste substance-supplying body 10K of the taste substance-supplying article 1K according to the $12^{th}$ embodiment of the present invention is brought into contact with tongue 6.

The taste substance-supplying article 1K according to the $12^{th}$ embodiment differs from the taste substance-supplying article 1H in the $9^{th}$ embodiment in that it is fixed to teeth 3 forming a portion having no taste receptor in the oral cavity. Configurations other than this are the same as those in the $9^{th}$ embodiment, and thus explanation for the same members is omitted.

The taste-releasing parts and the taste substance composing the taste substance-supplying body 10K are composed of the same materials as those of taste-releasing parts and the taste substance in the $9^{th}$ embodiment. Similarly, the fixing part is composed of the same material as that of the fixing part in the $9^{th}$ embodiment. The taste substance-supplying body 10K has a size almost the same as that of one tooth. An adhesive composing the fixing part is provided on the surface of the taste substance-supplying body 10K, thereby fixing the taste substance-supplying body 10K to the medial surface of the teeth 3.

In order to sense the taste from a taste substance when a user of the taste substance-supplying article 1K has a meal, the user moves tongue 6 to come into contact with the taste substance-supplying article 1K. Accordingly, the taste-releasing parts are dissolved because of water contained in saliva adhering to the tongue 6, the taste substance is released from the taste-releasing parts to come into contact with taste receptors, and then the user of the taste substance-supplying article 1K senses the taste from the taste substance.

With the taste substance-supplying article 1K according to the $12^{th}$ embodiment, the following effects can be obtained.

The taste substance-supplying body of the taste substance-supplying article 1K is fixed to teeth 3 forming a part the oral cavity having no taste receptor. With this configuration, when a user of the taste substance-supplying article 1K wants to sense the taste from a taste substance, the user moves tongue 6 to be in contact with the taste substance-supplying article 1K, so that the user can sense the taste from the taste substance. In contrast, when a user of the taste substance-supplying article 1K does not want to sense the taste from a taste substance, the taste-releasing part of the taste substance-supplying article 1K is not brought into contact with taste receptors of the user of the taste substance-supplying article 1K, creating a state of sensing no taste.

Figure 17:
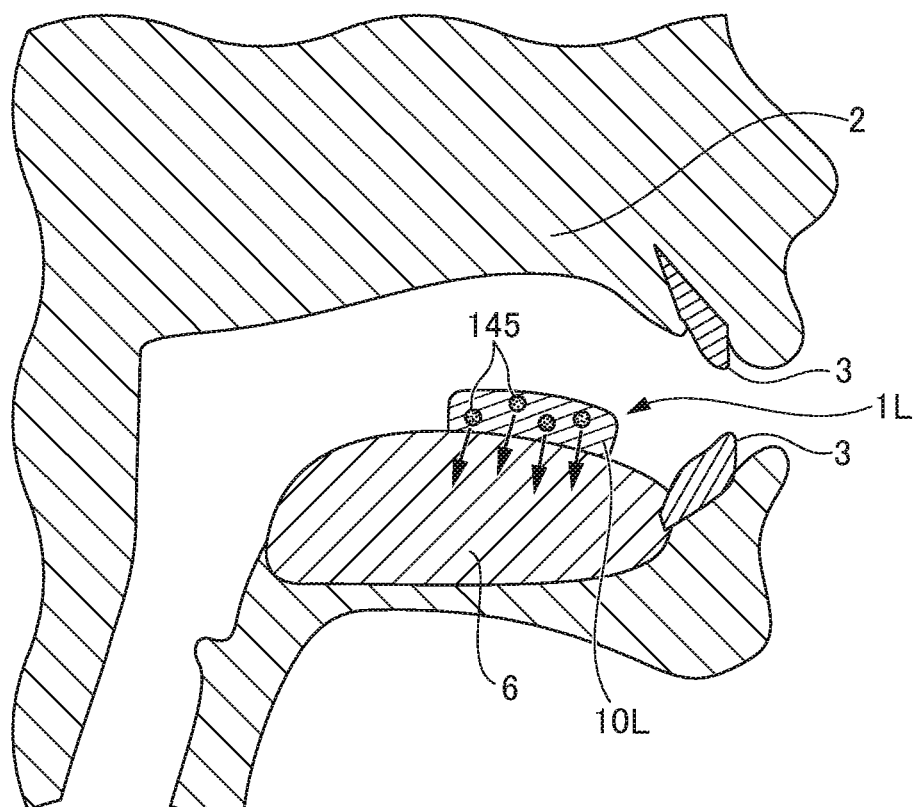
FIG. 17 is a schematic sectional view showing how a taste substance-supplying body 10L of a taste substance-supplying article 1L according to a thirteenth embodiment of the present invention is fixed to tongue 6.

Next, a taste substance-supplying article 1L according to the $13^{th}$ embodiment will be explained referring to FIG. 17. FIG. 17 is a schematic sectional view showing how the taste substance-supplying body 10L of the taste substance-supplying article 1L according to the $13^{th}$ embodiment the present invention is fixed to tongue 6.

The taste substance-supplying article 1L according to the $13^{th}$ embodiment differs from the taste substance-supplying article 1H in the $9^{th}$ embodiment in that the taste-releasing part is composed of a cohesive material and also composes a fixing part. Configurations other than this are the same as those in the $9^{th}$ embodiment, and thus explanation for the same members is omitted.

The taste substance-supplying article 1L having a taste substance, a taste-releasing part, and, a fixing part is composed of a cohesive substance such as high-polymer polyethylene glycol and the taste substance, which are dispersed in a base composed of Vaseline, beeswax, macrogol or the like. The taste substance is composed of the same material as that of the taste substance in the $9^{th}$ embodiment. With this configuration, the taste substance-supplying article 1L has adhesiveness at the ordinary temperature, and is gelatinous like ointment. Accordingly, the taste substance-supplying article 1L having the taste-releasing part, the taste substance, and, the fixing part is applied and fixed to tongue 6 or the like is used.

Alternatively, the taste substance-supplying article 1L is composed of a film-like solid substance. Specifically, the taste substance-supplying article 1L is composed of a mixture of a cohesive substance such as high-polymer polyethylene glycol and a taste substance. Accordingly, the taste substance-supplying article 1L having the taste-releasing part, the taste substance, and, the fixing part is used while being bonded to and fixed to tongue 6 or the like.

When the taste substance-supplying article 1L fixed to the tongue 6 is brought into contact with saliva adhering to taste receptors 2010, the taste-releasing part is dissolved in the oral cavity because of water contained in saliva, the taste substance 145 is brought into contact with taste receptors existing on the tongue 6, so that a user of the taste substance-supplying article 1L senses the taste from the taste substance.

According to the taste substance-supplying article 1L of the $13^{th}$ embodiment, the following effects can be obtained. The taste substance-supplying article 1L is composed of a soluble and cohesive taste-releasing part and a fixing part. With this configuration, the taste substance-supplying article 1L can be easily applied or bonded, and fixed to a part of palate 2, so that convenience of the taste substance-supplying article 1L can be enhanced.

Examples

Next, the above taste substance-supplying article 1K according to the $12^{th}$ embodiment was actually produced and a test was conducted for testing the effects. In this test, the taste substance-supplying article 1K composed by laminating a rectangular parallelepiped-shaped taste substance-supplying body and a rectangular parallelepiped-shaped fixing part was used. The size of the taste substance-supplying body is 16 mm long, 6 mm wide, and 2 mm thick. The size of the fixing part is 16 mm long, 6 mm wide, and 1 mm thick. The taste substance-supplying body has sodium chloride as a taste substance. The amount of sodium chloride contained per taste substance-supplying article 1K is about 150 mg. The taste substance-supplying article 1K was produced by the following steps.

Preparation of Cohesive Layer (Fixing Part)

First, 10 g of polyethylene glycol (molecular weight: 1000) was heated and melted. 2 g of polyethylene oxide (molecular weight: 4000000) and 2 g of CMC-Na (molecular weight: 700000) were stirred with a high-speed mixer for 5 minutes, and then the mixture was added to and mixed with the melted product. The resulting mixture was poured into a silicone template, and then cooled at 2° C. for 30 minutes, thereby preparing a cohesive layer.

Preparation of Gustatory Layer (Taste Substance-Supplying Body)

8.5 g of polyethylene glycol (molecular weight: 1000), 1.5 g of polyethylene glycol (molecular weight: 2000), 2.4 g of CMC-Na (molecular weight: 90000), 10 g of sodium chloride and 3 mL of pure water were stirred and mixed with a high-speed mixer for 20 minutes. The mixture was poured into a silicone template, heated at 60° C. for 2 hours, and then dried, thereby preparing a gustatory layer.

Subsequently, the thus prepared gustatory layer was heated and melted at 60° C., the cohesive layer is caused to come into contact with the gustatory layer, and then the layers were cooled at 2° C. for 30 minutes, thereby bonding the gustatory layer to the cohesive layer. In the test, the prepared taste substance-supplying article 1K was immersed in water for 5 seconds, and the cohesive layer was bonded behind the lower front tooth 3 as shown in FIG. 16. A subject can sufficiently sense a moderate salty taste for about 10 minutes by licking the gustatory layer while having the salt-free food or drink. Accordingly, a subject can sense a saltiness sufficiently by licking a small amount of sodium chloride in the gustatory layer, although the subject eats a completely-salt-free food or drink.

The present invention is not limited to the above embodiments, and can be varied within the technical scope described in claims. For example, in the $1_{st}$ embodiment, the taste substance-supplying article 1 has a pair of bridge parts 81, but its configuration is not limited thereto. For example, the reservoir part-supporting part may be composed of only one of bridge parts as in the $2^{nd}$ embodiment. Specifically, the taste substance reservoir part may be fixed to one end of the reservoir part-supporting part, and the other end of the reservoir part-supporting part may be fixed to a part of the oral cavity. Similarly, in the $5^{th}$ embodiment, the taste substance-supplying article 1D has a pair of bridge parts 81D, but its configuration is not limited thereto. The reservoir part-supporting part may be composed of only one of the bridge parts as in the $2^{nd}$ embodiment.

Conversely, in the $2^{nd}$ embodiment, the taste substance-supplying article 1A has, not a pair of, but only one of bridge parts 81A, however, its configuration is not limited thereto. If a false tooth is inserted also on the right side of palate 2, as in the $1^{st}$ embodiment and $5^{th}$ embodiment, a taste substance-supplying article is composed to have a pair of bridge parts and then the other bridge part may be fixed to the false tooth on the right side of the palate 2.

Furthermore, the taste-releasing part is composed of the porous membrane 13, but its configuration is not limited thereto. For example, the taste-releasing part may be composed of an opening and a porous material disposed within the reservoir space 12. In this case, the porous material is impregnated with the taste substance 145. As a porous material, for example, sponge, kaimen, or the like can be used. Moreover, in addition to the use of such a porous material, drug delivery or the like to be used for an anti-cancer agent or the like can also be used. Here, the term "drug delivery" means a material that is designed to the gradual release (sustained release) of a pharmaceutical preparation appropriately within a predetermined time. For example, candies and the like are made not to be melted quickly but to be gradually melted over a long time, and such products are also included in examples of the drug delivery.

Furthermore, in the $6^{th}$ embodiment, the acceleration sensor 61 is used for detecting the chewing of a food or drink by a user of the taste substance-supplying article 1E, but its configuration is not limited thereto. Moreover, the vibration sensor 62 is used for detecting a food or drink taken into the oral cavity of a user of the taste substance-supplying article 1E is used, but its configuration is not limited thereto.

Furthermore, in the $6^{th}$ embodiment, the taste substance-supplying article 1E is removed from the palate 2, so as to complete the control by the control part 51, but its configuration is not limited thereto. For example, with the use of a timer, the control by the control part 51 may be completed 10 minutes, for example, after the detection of the first intake of a food or drink into the oral cavity.

Furthermore, in the $6^{th}$ embodiment, as a mechanism for controlling the gradual release (exudation) of the taste substance 145 from the porous membrane 13, the mechanism that involves driving the actuator 133E to vary the pore size of the porous membrane 13 within the range of 1 nm-10 nm, so as to increase or decrease the pore size, and gradually releasing the taste substance 145 accommodated within the reservoir space 12 from the taste-releasing part is employed, but its configuration is not limited thereto. For example, a mechanism that can also be employed herein has a configuration wherein pressure can be applied by an actuator to a taste substance impregnated material, and involves determining the amount of exudation by adjusting pressure to be applied to the taste substance impregnated material as in the $5^{st}$ embodiment, and causing the taste substance to reach the top surface of the porous membrane through relatively large pores of the porous membrane.

Furthermore, in the $7^{th}$ embodiment, in order to atomize the taste substance 145, a piezoelectric material (piezoelectric vibrator) is used for generating surface acoustic wave (SAW), but its configuration is not limited thereto. The taste substance 145 can also be atomized with other configurations.

An instrument for attachment to teeth such as a dental brace 6D or a false tooth 4A is used as an attachment member to be fixed to a part of the oral cavity, but the example thereof is not limited thereto. For example, as an attachment member, an implant (artificial tooth root) may also be used. In addition, the shape and configuration of each part of the taste substance-supplying article are not limited to those of the embodiment. In addition, the taste-releasing part may also be composed so as to release the taste substance 145 by absorbing water.

Furthermore, the material(s) to be used for each configuration of the taste substance-supplying article is not limited to a material used in each configuration of the above embodiments. For example, in the $9^{th}$ embodiment, or the like, the taste-releasing parts 13H are composed of a material that is gradually dissolved, but the examples of the material are not limited thereto. For example, the taste-releasing part may also be composed of a material that can be disintegrated in the oral cavity. In this case, the taste-releasing part may be entirely disintegrated, or may have a configuration such that its framework portion is not disintegrated to maintain the shape, but the other portions are disintegrated. Such a disintegratable taste-releasing part may be composed of an edible and/or drinkable material.

Furthermore, in the $9^{th}$ embodiment or the like, the taste-releasing parts 13H are composed of a material that is gradually dissolved when it is brought into contact with saliva, but the example thereof is not limited thereto. For example, the taste-releasing part may be gradually dissolved or disintegrated via contact with another chemical substance other than water, or action by heat, light, magnetic field, pressure, mechanical force, or the like. Moreover, for example, the taste-releasing part may be composed of a material that is fixed to a part of the oral cavity and allows the taste-releasing part to be dissolved after a predetermined time.

Furthermore, in the 9$^{th}$ embodiment or the like, the taste substance-supplying body composed of the taste-releasing parts 13H and the fixing part 80H may be coated. For example, the taste substance-supplying body composed of the taste-releasing parts 13H and the fixing part 80H may be coated with a silicone film, for example. Therefore, the film is peeled off when the taste substance-supplying body is used, so as to expose a cohesive substance composing the fixing part, cause the exposed cohesive substance to come into contact with a part of the oral cavity, and then fix the taste substance-supplying body to the part of the oral cavity. Moreover, the taste-releasing parts 13H are each coated with an edible substance (e.g., ethyl cellulose) if necessary, so that the elution of the taste substance 145 contained in the taste-releasing parts 13H may be prevented. Moreover, the taste substance-supplying body composed of the taste-releasing parts 13H and the fixing part 80H may also be coated with a material that is dissolved or disintegrated when it is brought into contact with saliva or the like. Moreover, the cohesive substance composing the fixing part is not limited to fix the taste substance-supplying body to a part of the oral cavity. For example, the cohesive substance composing the fixing part may fix the reservoir part-supporting part to a part of the oral cavity.

Furthermore, in the 10$^{th}$ embodiment or the like, the fixing part 80I may be coated with an edible substance (e.g., ethyl cellulose), if necessary. Accordingly, this can prevent the taste substance-supplying body 10I from leaving from the fixing part 80I after adhesion of the fixing part 80I to undesired intraoral sites or a food or drink.

Furthermore, in the 9$^{th}$ embodiment and the 10$^{th}$ embodiment, the taste substance-supplying articles 1H and 1I are fixed to palate 2, but may be fixed to any site other than the palate 2. The taste substance-supplying articles 1H and 1I may be fixed to a part of the oral cavity.

Furthermore, in the taste substance-supplying article 1J according to the 11$^{th}$ embodiment, the taste substance-supplying body 10J is disposed covering tongue 6, so as to surround almost the entire tongue 6, but its configuration is not limited thereto. For example, the taste substance-supplying body 10J may be disposed to any portion among the entire area of the oral cavity.

Furthermore, in the taste substance-supplying article 1J according to the 11$^{th}$ embodiment, taste substance-supplying body is net-shaped, but its configuration is not limited thereto. For example, the taste substance-supplying article 1H according to the 9$^{th}$ embodiment may have a configuration, in which a through-hole that passes through in the vertical direction in FIG. 13 is formed. With this configuration, a user of the taste substance-supplying article can sense during the meal, via the through-hole, the taste of a food the user is actually eating, together with the taste from the taste substance 145 because of the taste receptors.

Moreover, the configuration of the net-shaped taste-substance-supplying article is not limited to the configuration of the taste substance-supplying article 1J according to the 11$^{th}$ embodiment. For example, the taste substance-supplying body of the net-shaped taste substance-supplying article may be entirely covered by a fixing part and fixed to a part of the palate in a manner similar to that in the 10$^{th}$ embodiment, or, may be applied to a part of the palate in a manner similar to that in the 13$^{th}$ embodiment or bonded to a part of the palate.

Furthermore, in the 12$^{th}$ embodiment, the taste substance-supplying body 10K composed of the taste-releasing part and the fixing part is fixed to the medial surface of a tooth 3 with an adhesive composing the fixing part, but its configuration is not limited thereto. The taste substance-supplying body may be fixed to a portion of an area being a part of the oral cavity and having no taste receptors, such as a portion that does not cause any obstacle for the user to have a meal (e.g., parts inside of the lips, and parts at the back of the inside of the cheeks).

EXPLANATION OF REFERENCE NUMERALS 1, 1A, 1B, 1C, 1D, 1E, 1F, 1G, 1H, 1I, 1J, 1K, 1L Taste substance-supplying article
2 Palate
4A False tooth
6 Tongue
6D Dental brace
10, 10A, 10B, 10C, 10D Taste substance reservoir part
10I, 10J, 10K, 10L Taste substance-supplying body
11 Reservoir
12 Reservoir space
13 Porous membrane (taste-releasing part)
14 Taste substance impregnated material
80, 80A, 80C, 80D, 80F, 80G Reservoir part-supporting part
80H Taste-releasing portion
111 Opening part
145 Taste substance
2010 Taste receptors

The invention claimed is:
1. A taste substance-supplying device, comprising:
a seasoning, an amount of which is substantially smaller than an amount that is normally desired;
a taste-releasing part configured to retain the seasoning and to release the seasoning; and
a fixing part, formed with an adhesive, and configured to fix the taste-releasing part in an oral cavity so that the taste-releasing part can be in contact with at least a portion of taste receptors located within the oral cavity, wherein the taste-releasing part directly supplies the seasoning to the taste receptors.
2. The taste substance-supplying device according to the claim 1, wherein the seasoning provides one of a salty taste, a sweet taste, a sour taste and an umami taste.
3. The taste substance-supplying device according to the claim 1, wherein the amount of the seasoning is about 150 mg.
4. The taste substance-supplying device according to the claim 1, wherein the amount of the seasoning is about 80 mg.
5. The taste substance-supplying device according to the claim 1, wherein the adhesive includes CMC-Na.

* * * * *